(12) United States Patent
Veryasov et al.

(10) Patent No.: US 11,840,509 B2
(45) Date of Patent: Dec. 12, 2023

(54) PROCESS TO CONDUCT AN ENDOTHERMIC DEHYDROGENATION AND/OR AROMATISATION REACTION IN A FLUIDIZED BED REACTOR

(71) Applicant: TOTALENERGIES ONETECH, Courbevoie (FR)

(72) Inventors: Gleb Veryasov, Nivelles (BE); Nikolai Nesterenko, Nivelles (BE); Walter Vermeiren, Houthalen (BE)

(73) Assignee: TOTALENERGIES ONETECH, Courbevoie (FR)

( * ) Notice: Subject to any disclaimer, the term of this patent is extended or adjusted under 35 U.S.C. 154(b) by 0 days.

(21) Appl. No.: 18/017,070

(22) PCT Filed: Jul. 27, 2021

(86) PCT No.: PCT/EP2021/071026
§ 371 (c)(1),
(2) Date: Jan. 19, 2023

(87) PCT Pub. No.: WO2022/023355
PCT Pub. Date: Feb. 3, 2022

(65) Prior Publication Data
US 2023/0295062 A1 Sep. 21, 2023

(30) Foreign Application Priority Data

Jul. 28, 2020 (EP) ..................... 20315366

(51) Int. Cl.
*C07C 5/333* (2006.01)
*B01J 8/42* (2006.01)
*B01J 8/18* (2006.01)

(52) U.S. Cl.
CPC .......... *C07C 5/3337* (2013.01); *B01J 8/1827* (2013.01); *B01J 8/1836* (2013.01); *B01J 8/42* (2013.01);
(Continued)

(58) Field of Classification Search
CPC .............. C07C 5/3337; C07C 2523/12; C07C 2523/14; C07C 2523/36; C07C 2523/42;
(Continued)

(56) References Cited

U.S. PATENT DOCUMENTS

| 3,499,947 A | 3/1970 | Johnson |
| 2002/0007594 A1 | 1/2002 | Muradov |

FOREIGN PATENT DOCUMENTS

WO 2019/145279 A1 8/2019

OTHER PUBLICATIONS

International Search Report dated Oct. 15, 2021 issued in corresponding International Application No. PCT/EP2021/071026.
(Continued)

*Primary Examiner* — Thuan D Dang
(74) *Attorney, Agent, or Firm* — Nath, Goldberg & Meyer; Joshua B. Goldberg

(57) ABSTRACT

The disclosure relates to a process to perform an endothermic dehydrogenation and/or aromatization reaction of hydrocarbons, said process comprising the steps of providing at least one fluidized bed reactor comprising at least two electrodes and a bed comprising particles; putting the particles in a fluidized state to obtain a fluidized bed; heating the fluidized bed to a temperature ranging from 480° C. to 700° C. to conduct the reaction; and obtaining a reactor effluent containing hydrogen, unconverted hydrocarbons, and olefins and/or aromatics; wherein the particles of the bed comprise electrically conductive particles and particles of a catalytic composition, wherein at least 10 wt. % of the particles are
(Continued)

electrically conductive particles and have a resistivity ranging from 0.001 Ohm·cm to 500 Ohm·cm at 500° C. and wherein the step of heating the fluidized bed is performed by passing an electric current of through the fluidized bed.

20 Claims, 3 Drawing Sheets

(52) U.S. Cl.
CPC ............... *B01J 2208/00398* (2013.01); *B01J 2208/00805* (2013.01); *B01J 2208/00902* (2013.01); *C07C 2523/12* (2013.01); *C07C 2523/14* (2013.01); *C07C 2523/36* (2013.01); *C07C 2523/42* (2013.01); *C07C 2523/44* (2013.01); *C07C 2523/46* (2013.01); *C07C 2523/50* (2013.01); *C07C 2523/52* (2013.01)

(58) Field of Classification Search
CPC ............ C07C 2523/44; C07C 2523/46; C07C 2523/50; C07C 2523/52; B01J 8/1827; B01J 8/1836; B01J 8/42; B01J 2208/00398; B01J 2208/00805; B01J 2208/00902
See application file for complete search history.

(56) References Cited

OTHER PUBLICATIONS

International Preliminary Report on Patentability dated Oct. 20, 2022 issued in corresponding International Application No. PCT/EP2021/071026.

Annex of International Preliminary Report on Patentability dated Aug. 29, 2022.

PROCESS TO CONDUCT AN ENDOTHERMIC DEHYDROGENATION AND/OR AROMATISATION REACTION IN A FLUIDIZED BED REACTOR

This is a National Phase Application filed under 35 U.S.C. 371 as a national stage of PCT/EP2021/071026, filed Jul. 27, 2021, an application claiming the benefit of European Application No. 20315366.3, filed Jul. 28, 2020, the content of each of which is hereby incorporated by reference in its entirety.

TECHNICAL FIELD

The present disclosure relates to a process for performing an endothermic dehydrogenation and/or aromatisation reaction in an installation comprising at least one fluidized bed reactor, the process is performed without the need of an external heating device in the said fluidized bed reactor. The present disclosure aims to contribute to the replacement of the use of fossil carbon-based fuels heating devices. The present disclosure relates to the electrification of the chemical industry.

TECHNICAL BACKGROUND

Climate change and ongoing energy transition make it mandatory to replace fossil carbon-based fuels in chemical production and recycled processes with a more environmentally friendly decarbonized source of energy. Transforming hydrocarbons into valuable chemicals requires elevated temperatures, often higher than 450° C. and even up to 1000° C. and are often endothermic. The energy needed is, therefore, high and not often environmentally friendly, as is demonstrated by the common use of fired heated reactors. Several studies have been undertaken to reduce the burden imposed by these (harsh) reaction conditions.

The study of Asensio J. M. et al., entitled "Hydrodeoxygenation using magnetic induction: high-temperature heterogeneous catalysis in solution" (Angew. Chem. Int. Ed., 2019, 58, 1-6) describes the use of magnetic nanoparticles as heating agents to improve the energy efficiency of reactions performed at high temperature, as the heat can be then directly and homogeneously transferred to the medium without the need for heating the reactor walls. This was applied in the hydrodeoxygenation of ketones. However, in such a system, relatively low temperatures up to 280° C. were reached and the reaction is exothermic.

In the study of Wismann S. T. et al., entitled "Electrified methane reforming: A compact approach to greener industrial hydrogen production" (Science, 2019, 364, 756-759), a conventional fired reactor was replaced by an electric-resistance-heated reactor. A laboratory-scale reactor based on FeCrAl alloy tube having a diameter of 6 mm and coated with a 130-μm nickel-impregnated washcoat was used to carry out steam methane reforming. As the heat source and the wall of the tube are one, it is possible to minimize the loss of heat and then to render more efficient and more economical the process of steam methane reforming. Temperatures with a maximum of 500° C. were reached with this kind of reactor.

In the study of Malerød-Fjeld H. et al., entitled "Thermo-electrochemical production of compressed hydrogen from methane with near-zero energy loss" (Nat. Energy, 2017, 2, 923-931), a ceramic tube, having an outer diameter of 1 cm and made of a perovskite derivative, is used as the electrolyte. By applying a voltage and hence a current across the electrolyte, hydrogen can be selectively extracted from methane and steam. The perovskite derivative is supplemented with nickel nanoparticles to provide the catalyst necessary for the reaction.

In the study of Varsano F. et al., entitled "Dry reforming of methane powered by magnetic induction" (Int. J. of Hydrogen Energy, 2019, 44, 21037-21044), electromagnetic induction heating of catalytic heterogeneous processes was used and has been demonstrated as bringing several advantages in terms of process intensification, energy efficiency, reactor setup simplification and safety issues coming from the use of radiofrequency. Temperatures ranging between 850° C. and 900° C. in reactors having 1 cm of inner diameter can be reached using $Ni_{60}Co_{60}$ pellets as heat mediators in a continuous-flow fixed-bed reactor.

These examples show that progress exists in the field of transforming fossils sources into valuable chemicals with the perspective to diminish the impact on the climate. However, this progress has not been developed to a large scale as it is rather limited to the laboratory environment.

With regards to this matter, the Shawinigan process, described in CA 573348, relates to a process to prepare hydrocyanic acid from ammonia using in a fluidized bed reactor made of high temperature-resistant silica glass and comprising conductive carbon particles, such as coke and/or petroleum coke. The principle resides in that the electricity is used to heat the conductive carbon particles which can maintain the fluidized bed at a temperature sufficient to transform ammonia into hydrocyanic acid, which is then recovered from the outgoing gas coming off the fluidized bed. The inner diameter of the reactor tube was 3.4 cm. A temperature ranging between 1300° C. and 1600° C., sufficient to perform the requested reaction, can be reached by using such conductive carbon particles.

U.S. Pat. No. 2,982,622 describes a method for producing hydrogen and high quality coke which comprises passing inert solid particles as a relatively dense mass downwardly through an elongated reaction zone, applying an electrical voltage of 0.1 to 1000 volts per inch across at least a portion of said solids mass in said reaction zone, said voltage being sufficient to raise the temperature of said solids to 1800 to 3000 F. due to their resistance to the flow of electricity without causing substantial electrical spark discharges through said solids mass, downwardly withdrawing thus heated solids from said reaction zone, pre-heating a hydrocarbon feed by heat exchange with said withdrawn solids and introducing said preheated feed into and upwardly through said reaction zone in the form of an upwardly moving gasiform stream, said feed contacting said heated solids and being converted to light vapors including a substantial portion of hydrogen and carbon which deposits on said solids, heat exchanging hot vapors withdrawn from said reaction zone with inert solids in a heating zone, circulating at least a portion of the solids withdrawn from the reaction zone and previously heat exchanged with said feed to said heating zone, passing solids from said heating zone to said reaction zone as solids feed thereto, and recovering at least a portion of the solids withdrawn from the reaction zone as product and recovering hydrogen gas and light vapors from the upper portion of said reaction zone.

U.S. Pat. No. 3,259,565 describes a process for converting hydrocarbons to produce lower boiling hydrocarbons and solid coke particles of a size larger than fluidizable size which comprises passing coke agglomerates down through a hot fluidized bed of coke particles, introducing hydrocarbon oil feed into said fluidized bed to crack the hydrocarbon oil, passing cracked vaporous products overhead, removing coke agglomerates from said fluid bed and passing them down through a heat exchanger zone in counter-current contact with said withdrawn cracked vaporous products to cool said cracked vaporous products and to heat said coke agglomerates while condensing and depositing higher boiling hydrocarbons from said cracked vaporous products on said coke agglomerates, withdrawing resulting cracked vaporous products as product, recirculating the so treated coke agglomerates a number of times through said heat exchange zone to deposit hydrocarbons and through said hot fluidized coke bed to coke the deposited high boiling hydrocarbons and to increase the size of the coke agglomerates, withdrawing coke agglomerates of increased size as product from the system.

The disclosure of US 2017/0158516 described a fluidized-bed reactor made of silicon carbide for preparing granular polycrystalline silicon at the industrial level. The fluidized-bed reactor is heated using a heating device which is placed in an intermediate jacket between the outer wall of the reactor tube and the inner wall of the reactor vessel. Such intermediate jacket comprises an insulation material and is filled or flushed with an inert gas. It was found that the use of sintered silicon carbide (SSiC) having a SiC content of 98% by weight as the main element of the reactor tube with a high purity SiC coating deposited by chemical vapour deposition allowed reaching high temperature up to 1200° C. without the tube being corroded. It was also found that using siliconized silicon carbide (SiSiC) as the main element of the reactor tube without any surface treatment, such as the deposition of a coating layer, led to the tube being corroded.

On the other hand, the disclosure of Goldberger W. M. et al., entitled "*The electrothermal fluidized bed*" (*Chem. Eng. Progress*, 1965, 61 (2), 63-67, relates to fluidized-bed reactor made in graphite and susceptible to perform reactions such as the hydrocracking of hydrocarbons, the pyrolysis of organics, the production of elemental phosphorus or the chlorination of zirconium oxide. Operation at temperatures up to about 4400° C. appears possible. However, it is not certain that from the long-term perspective, the graphite material used to design the fluidized-bed reactor can resist such harsh reaction conditions. Indeed, in the study of Uda T. et al., entitled "*Experiments on high temperature graphite and steam reactions under loss of coolant accident conditions*", (*Fusion Engineering and Design*, 1995, 29, 238-246), it has been shown that graphite corrodes under conditions involving steam and elevated temperature, for instance between 1000° C. and 1600° C. Also, as shown in the study of Qiao M-X. et al., entitled "*Corrosion of graphite electrode in electrochemical advanced oxidation processes: degradation protocol and environmental application*", (*Chem. Eng. J.*, 2018, 344, 410-418), the graphite is susceptible to carbon oxidation reaction, which impacts its activity as an electrode by restricting notably the voltage that can be applied to it.

The present disclosure aims to provide a large-scale solution to one or more of the problems encountered in the prior art that is suitable for application in the industry, such as the chemical industry. The present disclosure aims to contribute to the replacement of the use of fossil carbon-based fuels heating devices in fluidized bed reactors.

The present disclosure provides a solution to conduct endothermic dehydrogenation and/or aromatisation reactions of hydrocarbons into a mixture of hydrogen and olefins or aromatics. Dehydrogenation to introduce double carbon bonds in hydrocarbons is an important process to make ethylene, propylene, butenes, butadiene, pentadienes, isoprene and styrene. These dehydrogenation reactions, requiring catalysts to proceed are very endothermic resulting in temperature drop when the reaction progresses when operated under adiabatic conditions. Propane dehydrogenation is practised at a large industrial scale in processes that are designed in particular to introduce the required reaction heat operating at a temperature between 550 and 650° C. and low pressure (reaction is equilibrium limited):

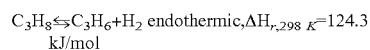
$C_3H_8 \leftrightarrows C_3H_6+H_2$ endothermic,$\Delta H_{r,298\ K}$=124.3 kJ/mol One well-known "on-purpose" process to produce propylene, the Oleflex process (OLEFLEX is a trademark of UOP Inc.) employing multiple adiabatic reactors arranged in a series, wherein propane dehydrogenation is catalysed by catalyst based on a Pt—Sn/alumina catalyst in moving-bed reactors under nearly atmospheric pressure and temperatures of 580-650° C. Inter-heaters are used between reactors to maintain the desired reactor temperatures while hydrogen and traces of sulfur are injected into the reactor system to suppress the formation of coke. As the catalyst still slowly deactivate, the dehydrogenation reactor is a moving catalyst bed reactor where the catalyst moves slowly under gravity from the top to the bottom of the reactor vessel and at the bottom is sent to a regenerator. In the regenerator, the catalyst is decoked with air and reactivation with chlorine which serves to redisperse the platinum. This reactor technology is called Continuous Catalytic Regeneration (CCR is a trademark of UOP). The various aspects of the OLEFLEX™ reaction system, are disclosed in several publications such as U.S. Pat. Nos. 5,227,566, 5,457,077, 5,177, 293, 5,227,567 and 8,563,793. Disadvantages of the OLEFLEX™ reaction system, however, may include the production of $CO_2$ during combustion of fuel in the preheaters and inter-heaters and the complex nature of the reactor equipment. The OLEFLEX™ has also a variant for butane dehydrogenation.

Another well-known "on-purpose" process to produce propylene, the "CATOFIN™ process" (CATOFIN is a trademark of ABB Lummus Global) that includes multiple parallel fixed bed dehydrogenation reactors, using a chromium-containing catalyst. Aspects of the CATOFIN™ process are described in WO1995023123 and U.S. Pat. No. 5,315,056. The required reaction heat is introduced by employing a cyclic process: hot catalyst, $Cr_2O_3/Al_2O_3$ catalyst, is contacted with the propane during a few minutes while the temperature drops as the dehydrogenation proceeds, followed by purging the reactor and burning the deposited coke or added fuel to reactivate and reheat the catalyst, bringing the catalyst ready for the next propane dehydrogenation cycle. By putting several of such reactors in parallel that are each in a different state of the cycle, a nearly continuous propane process can be operated. Disadvantages of the CATOFIN™ process include the need for a relatively high catalyst inventory due to its use of a fixed bed configuration and the requirement for high frequency, high-temperature valves for swapping the fixed beds, next to the production of $CO_2$ during preheating of the feedstock and reheating of the catalyst. The CATOFIN™ has also a variant for butane dehydrogenation and pentane dehydrogenation.

Another type of dehydrogenation reactor, using a fluidized bed reactor is described in U.S. Pat. Nos. 8,669,406, 6,362,385, 4,746,643, and 7,235,706. U.S. Pat. No. 5,430, 211 describes a dehydrogenation catalyst comprising a mordenite zeolite, further optionally including gallium, zinc or a platinum group metal.

Styrene is produced by dehydrogenation reaction of ethylbenzene:

$C_6H_5CH_2CH_3 \leftrightarrows C_6H_5CH=CH_2+H_2$ endothermic, $\Delta H_{r,298\ K}$=125 kJ/mole Thus, both an increase in temperature and a low pressure lead to higher conversion. The dehydrogenation of ethylbenzene is normally carried out with steam as a diluent and under reduced pressure. For dehydrogenation of ethylbenzene for production of styrene, the current state of the art industrial processes is conducted by using a $K_2O$-promoted iron oxide catalyst in fixed bed reactors and with water/steam as carrier gas (diluent) and carbon suppressor. Many other elements have a positive effect on iron-based catalysts like Mn, Co, Ni, Cu, Cr, alkaline earth, Al, V and Zn. Cr or Al are added to the catalyst for structural purposes while Ce enhances the activity and Mo the selectivity for styrene. Alkaline earth metal oxides improve stability while Cr and V stabilise against the reduction of iron oxide. A typical catalyst composition is 84% iron as $Fe_2O_3$, 2.5% chromium as $Cr_2O_3$ and 13% potassium as $K_2CO_3$. Steam is used in the dehydrogenation process as a heat carrier and is produced by energy-intensive evaporation generating large amounts of $CO_2$ by burning fuel. A large amount of steam is added to the ethylbenzene to suppress carbon formation on the catalyst, dilute the gas to lower the ethylbenzene partial pressure and favour the equilibrium and finally provide the heat of reaction by acting as a heat carrier.

Styrene production is either done in adiabatic or isothermal reactors:

Adiabatic reactor: fresh ethylbenzene feed is mixed with recycled ethylbenzene and vaporized and steam added. This stream is further heated by heat exchange with hot reactor effluent, superheated steam (produced in steam superheater furnace using fuel combustion) is added to bring the system up to reaction temperature (ca. 640° C.), and the stream is passed through the catalyst in the first adiabatic reactor where the temperature drops due to ethylbenzene conversion. Subsequently, the outlet stream is reheated before passage through the second reactor, generally using a heat-exchanger fed by superheated steam (in some cases three sequential reactors are used). Most adiabatic reactors are of the radial type to minimise pressure drop. Conversion of ethylbenzene can vary with the system but is often about 35 in the first reactor and 65% overall. Some units operate under vacuum, while others operate at low positive pressure. The steam to ethylbenzene ratio fed to the reactors is chosen to give optimum yield with minimum utility cost. The reactor effluent is fed through an efficient heat recovery system to minimize energy consumption, condensed, and separated into vent gas, a crude styrene hydrocarbon stream, and a steam condensate stream.

Isothermal dehydrogenation reactors are built like a shell-and-tube (multi-tubular) heat exchanger. Ethylbenzene and steam flow through the tubes, which are loaded with catalysts. The heat of the reaction is supplied by hot flue gas (BASF process) or by molten salts (alkali carbonates) (Lurgi process) on the shell side of the reactor-exchanger.

Catalytic reforming of naphtha in a refinery aims to produce high octane gasoline or aromatic rich cuts for aromatic extractions. Four typical reactions occur during catalytic reforming:

The dehydrogenation of naphthenes to convert them into aromatics and hydrogen:
Methylcyclohexane$\leftrightarrows$toluene+3 $H_2$ endothermic, $\Delta H_{r,298\ K}$=205 kJ/mole The isomerization of normal paraffins to isoparaffins, hydrogen neutral and nearly isothermic:
n-hexane→methyl-pentane $\Delta H_{r,298\ K}$=−4 kJ/mole The dehydrogenation and aromatization of paraffins to aromatics (commonly called dehydrocyclization), producing hydrogen:
Heptane→toluene+4 $H_2$ endothermic, $\Delta H_{r,298\ K}$=238 kJ/mole The hydrocracking of paraffins into smaller molecules, consuming hydrogen and exothermic.

During the catalytic reforming, the carbon number of the reactants remains unchanged, except for hydrocracking reactions which break down the hydrocarbon molecule by consuming hydrogen into lighter hydrocarbons, but this reaction is not desired in the refinery. The isomerization of normal paraffins does not consume or produce hydrogen. However, both the dehydrogenation of naphthenes and the dehydrocyclization of paraffins produce hydrogen. A semi-regenerative catalytic reformer (SRR) unit has typically three reactors (sometimes with an extra spare reactor, cyclic reformer) in series, each with a fixed bed of catalyst, while the catalyst is regenerated in situ during routine catalyst regeneration switch which occurs approximately once each 6 to 24 months. Continuous catalyst regeneration (CCR) reformers include a continuous in-situ regeneration of part of the catalyst in a separate regenerator, by using a radial moving bed reactor where the catalyst moves slowly by gravity through the reformer reactors and at the bottom of the last reactor the deactivated catalyst is transported to the regenerator. The different reactors with interheating can either be placed stacked-wise where the catalyst moves by gravity from one reactor to the next one or side-by-side where the catalyst is pneumatically transported from one reactor to the next.

The liquid naphtha feed is pumped up to the reaction pressure (5-45 atm) mixed with a hydrogen-rich recycle gas. The resulting liquid-gas mixture is preheated to total vaporization and heated to the reaction temperature (480-530° C.) before the vaporized reactants enter the first reactor. As the vaporized reactants flow through the fixed bed of catalyst in the reactor, the highly endothermic reactions occur and result in a large temperature decrease over the catalyst bed. To maintain the required reaction temperature and the rate of reaction, the vaporized stream is reheated in a subsequently fired heater before it flows to the next reactor. Usually, three or four reactors are all that is required to provide the desired performance of the catalytic reforming unit. The feed and intermediate streams are heated in a fired heater by combustion of fuel and hence generating a lot of $CO_2$.

The catalytic reforming catalysts are bifunctional, having both acidic and metallic functions. Typical catalysts that are mono-metallic, bi-metallic or tri-metallic catalysts supported on alumina, such as platinum (Pt/$Al_2O_3$), platinum-iridium (Pt—Ir/$Al_2O_3$) or platinum-iridium-tin (Pt—Ir—Sn/$Al_2O_3$) respectively. The metallic function serves the dehydrogenation reactions while both acid and metal serve the dehydrocyclisation and isomerisation reactions. The base reforming catalyst is platinum on chlorinated gamma alumina. Several promoters are added to improve its performance: rhenium and iridium improve stability whereas tin and germanium improve selectivity (less hydrogenolysis).

A particular selective reforming catalyst can convert $C_6$-$C_8$ paraffins into rich aromatics products. Non-acidic alkali or alkaline earth-exchange zeolite L (preferably KBaL) in combination with Group VIII (preferably Pt) and traces of halides inhibits undesired isomerization and hydrocracking reactions leading to enhanced aromatization selectivities. Besides the absence of acidity, the presence of highly dispersed Pt clusters inside the zeolite channels and the shape-selective effects imposed by the monodirectional channel structure (0.71 nm diameter) of the zeolite contribute to the excellent aromatization performance of Pt/KL catalysts. Modification of Pt/KL with rare earth elements improves the aromatization activity and the sulphur tolerance of the zeolite catalyst. Other mono-directional molecular sieves can be used as ZSM-12, zeolite omega, SAPO-5, SAPO-11. Suitable halides include chloride, fluoride, bromide, iodide, or combinations thereof. Suitable Group VIII metals include iron, cobalt, nickel, ruthenium, rhodium, palladium, osmium, iridium, and platinum. This highly endothermic aromatisation process is generally operated in radial moving bed reactors with continuous catalytic regeneration systems.

SUMMARY

According to a first aspect, the disclosure provides for a process to perform an endothermic dehydrogenation and/or aromatisation of hydrocarbons having at least two carbons to produce olefins and/or aromatics, said process comprising the steps of:
a) providing at least one fluidized bed reactor comprising at least two electrodes and a bed comprising particles;
b) putting the particles of the bed in a fluidized state by passing upwardly through the said bed a fluid stream to obtain a fluidized bed;
c) heating the fluidized bed to a temperature ranging from 480° C. to 700° C. to conduct an endothermic dehydrogenation and/or aromatisation reaction; and
d) obtaining a reactor effluent containing hydrogen, unconverted hydrocarbons and olefins and/or aromatics;
the process is remarkable in that the particles of the bed comprise electrically conductive particles and particles of a catalytic composition, wherein at least 10 wt. % of the particles based on the total weight of the particles of the bed are electrically conductive particles and have a resistivity ranging from 0.001 Ohm·cm to 500 Ohm·cm at 500° C.; wherein the catalytic composition comprises one or more metallic compounds; and in that the step (c) of heating the fluidized bed is performed by passing an electric current through the fluidized bed.

According to another definition, the disclosure provides for a process to perform an endothermic dehydrogenation and/or aromatisation of hydrocarbons having at least two carbons to produce olefins and/or aromatics, said process comprising the steps of:
a) providing at least one fluidized bed reactor comprising at least two electrodes and a bed comprising particles;
b) putting the particles of the bed in a fluidized state by passing upwardly through the said bed a fluid stream to obtain a fluidized bed;
c) heating the fluidized bed to a temperature ranging from 480° C. to 700° C. to conduct an endothermic dehydrogenation and/or aromatisation reaction; and
d) obtaining a reactor effluent containing hydrogen, unconverted hydrocarbons and olefins and/or aromatics;
the process is remarkable in that the particles of the bed comprise electrically conductive particles and particles of a catalytic composition, wherein at least 10 wt. % of the particles based on the total weight of the particles of the bed are electrically conductive particles and have a resistivity ranging from 0.001 Ohm·cm to 500 Ohm·cm at 500° C., in that the step (c) of heating the fluidized bed is performed by passing an electric current through the fluidized bed, and in that the catalytic composition comprises:
one or more catalyst materials selected from gallium, zinc, chromium, iron, metal of the group VIII or mixtures thereof, and one or more catalytic supports; or
from 50 to 85 wt. % of $Fe_2O_3$ based on the total weight of the catalyst composition; from 3 to 25 wt. % of $K_2O$; from 3 to 30 wt. % of $CeO_2$; from 0.1 to 5 wt. % of CaO; from 0.1 to 5 wt. % of $Na_2O$ and from 0.1 to 150 ppm of at least one element selected from Pb, Pt, Os, Ir, Ru, Re, Pd, Ag, Au, Sn or any mixture thereof; or
from 0.01 to 3.0 wt. % of one or more metals of the group VIII based on the total weight of the catalyst composition, from 0.1 to 3.5 wt. % of a halide; and from 0.01 to 5.0 wt. % of one or more metals selected from groups IIIA, IVA, IB, VIB and/or VIIB; or
from 5.0 to 90.0 wt. % of one or more zeolites comprising at least one 10-membered ring channel and based on the total weight of the catalyst composition, from 0.1 to 5.0 wt. % of a halide; and from 0.05 to 10.0 wt. % of one or more catalyst materials selected from Ga, In, Zn, Cu, Re, Mo, W; or from 0.005 to 1.0 wt. % of one or more metals of the group VIII or mixtures thereof based on the total weight of the catalyst composition.

For example, the process is selected from paraffin dehydrogenation process, an alkyl-aromatic dehydrogenation process, a naphtha reforming process and a paraffin aromatisation process.

According to another definition, the disclosure provides for a process to perform an endothermic dehydrogenation and/or aromatisation of hydrocarbons having at least two carbons to produce olefins and/or aromatics, wherein the process is selected from paraffin dehydrogenation process, an alkyl-aromatic dehydrogenation process, a naphtha reforming process and a a paraffin aromatisation process; said process comprising the steps of:
a) providing at least one fluidized bed reactor comprising at least two electrodes and a bed comprising particles;
b) putting the particles of the bed in a fluidized state by passing upwardly through the said bed a fluid stream to obtain a fluidized bed;
c) heating the fluidized bed to a temperature ranging from 480° C. to 700° C. to conduct an endothermic dehydrogenation and/or aromatisation reaction; and
d) obtaining a reactor effluent containing hydrogen, unconverted hydrocarbons and olefins and/or aromatics;
the process is remarkable in that the particles of the bed comprise electrically conductive particles and particles of a catalytic composition, wherein at least 10 wt. % of the particles based on the total weight of the particles of the bed are electrically conductive particles and have a resistivity ranging from 0.001 Ohm·cm to 500 Ohm·cm at 500° C., wherein the catalytic composition comprises one or more metallic compounds; and in that the step (c) of heating the fluidized bed is performed by passing an electric current through the fluidized bed.

Whatever is the definition selected, the fluid stream provided in step b) may comprise one or more hydrocarbons. For example, the fluid stream provided in step b) is a vaporized stream that comprises one or more hydrocarbons.

Surprisingly, it has been found that the use of electrically conductive particles such as silicon carbide, mixed oxides and/or mixed sulphides, said mixed oxides and/or said mixed sulphides being an ionic or mixed conductor, namely being doped with one or more lower-valent cations, in one or more fluidized bed reactors which are electrified allows maintaining a temperature sufficient to carry out an endothermic dehydrogenation and/or aromatization of hydrocarbons reaction requesting high-temperature conditions such as temperature reaction ranging from 480° C. to 700° C. without the need of any external heating device. The use of at least 10 wt. % of electrically conductive particles within the particles of the bed allows minimizing the loss of temperature when a voltage is applied. Thanks to the Joule effect, most, if not all, the electrical energy is transformed into heat that is used for the heating of the reactor medium.

In a preferred embodiment, the at least one fluidized bed reactor comprising at least two electrodes and a bed comprising particles is devoid of packing.

In a preferred embodiment, the volumetric heat generation rate is greater than 0.1 MW/m³ of fluidized bed, more preferably greater than 1 MW/m³, in particular, greater than 3 MW/m³.

In a preferred embodiment, the at least one fluidized bed reactor is devoid of heating means; for example, the at least one fluidized bed reactor comprises a vessel and is devoid of heating means located around or inside the vessel. For example, at least one fluidized bed reactor is devoid of heating means selected from ovens, gas burners, hot plates, or any combination thereof. For example, all the fluidized bed reactors are devoid of heating means selected from ovens, gas burners, hot plates, or any combination thereof.

In a preferred embodiment, the at least one fluidized bed reactor comprising at least two electrodes and a bed comprising particles is devoid of packing.

For example, the fluid stream comprising one or more hydrocarbons further comprises a hydrogen-containing gas and/or steam. For example, the fluid stream is a vaoprized stream that is comprising one or more hydrocarbons further comprises a hydrogen-containing gas and/or steam.

The solid particulate material (i.e. the particles) used in the fluidized bed reactor comprises solid particulates having electrical conductivity allowing generating heat and catalytic particulate material to catalyse the steam reforming of hydrocarbons. The catalytic particulate material can also be electrically conductive and hence contribute to the generation of heat for the endothermic dehydrogenation and/or aromatization of hydrocarbons reaction.

The Electrically Conductive Particles of the Bed

For example, the content of electrically conductive particles is ranging from 10 wt. % to 100 wt. % based on the total weight of the particles of the bed; preferably, from 15 wt. % to 95 wt. %, more preferably from 20 wt. % to 90 wt. %, even more preferably from 25 wt. % to 80 wt. % and most preferably from 30 wt. % to 75 wt. %. In the case where the content of electrically conductive particles based on the total weight of the particles of the bed is 100 wt. %, said electrically conductive particles are also catalytic particles.

For example, the content of electrically conductive particles based on the total weight of the bed is at least 12 wt. % based on the total weight of the particles of the bed; preferably, at least 15 wt. %, more preferably, at least 20 wt. %; even more preferably at least 25 wt. %; and most preferably at least 30 wt. % or at least 40 wt. % or at least 50 wt. % or at least 60 wt. %.

For example, the electrically conductive particles have a resistivity ranging from 0.005 to 400 Ohm·cm at 500° C., preferably ranging from 0.01 to 300 Ohm·cm at 500° C.; more preferably ranging from 0.05 to 150 Ohm·cm at 500° C. and most preferably ranging from 0.1 to 100 Ohm·cm at 500° C.

For example, the electrically conductive particles have a resistivity of at least 0.005 Ohm·cm at 500° C.; preferably of at least 0.01 Ohm·cm at 500° C., more preferably of at least 0.05 Ohm·cm at 500° C.; even more preferably of at least 0.1 Ohm·cm at 500° C., and most preferably of at least 0.5 Ohm·cm at 500° C.

For example, the electrically conductive particles have a resistivity of at most 400 Ohm·cm at 500° C.; preferably of at most 300 Ohm·cm at 500° C., more preferably of at most 200 Ohm·cm at 500° C.; even more preferably of at most 150 Ohm·cm at 500° C., and most preferably of at most 100 Ohm·cm at 500° C.

The selection of the content of electrically conductive particles based on the total weight of the bed and of the electrically conductive particles of a given resistivity influence the temperature reached by the fluidized bed. Thus, in case the targeted temperature is not attained, the person skilled in the art may increase the density of the bed particles, the content of electrically conductive particles based on the total weight of the particles of the bed and/or select electrically conductive particles with a lower resistivity to increase the temperature reached by the fluidized bed.

For example, the density of the solid particles in the bed is expressed as the void fraction. Void fraction or bed porosity is the volume of voids between the particles divided by the total volume of the bed. At the incipient fluidisation velocity, the void fraction is typically between 0.4 and 0.5. The void fraction can increase up to 0.98 in fast fluidised beds with lower values at the bottom of about 0.5 and higher than 0.9 at the top of the bed. The void fraction can be controlled by the linear velocity of the fluidising gas and can be decreased by recycling solid particles that are recovered at the top and send back to the bottom of the fluidized bed, which compensates for the entrainment of solid particles out of the bed.

The void fraction VF is defined as the volume fraction of voids in a bed of particles and is determined according to the following equation:

$$VF = \frac{Vt - Vp}{Vt} \quad (1)$$

wherein Vt is the total volume of the bed and is determined by $$Vt = AH \quad (2)$$

wherein A is the cross-sectional area of the fluidized bed and H is the height of the fluidized bed; and wherein Vp is the total volume of particles within the fluidized bed.

For example, the void fraction of the bed is ranging from 0.5 to 0.8; preferably ranging from 0.5 to 0.7, more preferably from 0.5 to 0.6. To increase the density of the particle bed, the void fraction is to be reduced.

For example, the particles of the bed have an average particle size ranging from 5 to 300 μm as determined by sieving according to ASTM D4513-11, preferably ranging from 10 to 200 μm and more preferably ranging from 20 to 200 μm or from 30 to 150 μm.

For example, the electrically conductive particles of the bed have an average particle size ranging from 5 to 300 μm as determined by sieving according to ASTM D4513-11, preferably ranging from 10 to 200 μm and more preferably ranging from 20 to 200 μm or from 30 to 150 μm.

For example, the electrically conductive particles of the bed are or comprise one or more particles selected from one or more metallic alloys, one or more non-metallic resistors, one or more metallic carbides, one or more transition metal nitrides, one or more metallic phosphides, one or more carbon-containing particles, one or more superionic conductors, one or more phosphate electrolytes, one or more mixed oxides being doped with one or more lower-valent cations, one or more mixed sulphides being doped with one or more lower-valent cations, and any mixture thereof.

In an embodiment, from 50 wt. % to 100 wt. % of the electrically conductive particles of the bed based on the total weight of the electrically conductive particles of the bed are one or more particles selected from one or more metallic alloys, one or more non-metallic resistors, one or more metallic carbides, one or more transition metal nitrides, one or more metallic phosphides, one or more carbon-containing particles, one or more superionic conductors, one or more phosphate electrolytes, one or more mixed oxides being doped with one or more lower-valent cations, one or more mixed sulphides being doped with one or more lower-valent cations, and any mixture thereof; preferably, from 60 wt. % to 100 wt. %; more preferably from 70 wt. % to 100 wt. %; even more preferably from 80 wt. % to 100 wt. % and most preferably from 90 wt. % to 100 wt. %.

With preference, the electrically conductive particles of the bed are or comprise one or more carbon-containing particles and one or more selected from one or more metallic alloys, one or more non-metallic resistors, one or more metallic carbides, one or more transition metal nitrides, one or more metallic phosphides, one or more superionic conductors, one or more phosphate electrolytes, one or more mixed oxides being doped with one or more lower-valent cations, one or more mixed sulphides being doped with one or more lower-valent cations, and/or any mixture thereof; with preference in a content of from 50 wt. % to 100 wt. % based on the total weight of the electrically conductive particles of the bed; preferably, from 60 wt. % to 100 wt. %; more preferably from 70 wt. % to 100 wt. %; even more preferably from 80 wt. % to 100 wt. % and most preferably from 90 wt. % to 100 wt. %.

As an alternative, the electrically conductive particles of the bed are or comprise one or more particles selected from one or more metallic alloys, one or more non-metallic resistors, provided that the non-metallic resistor is not silicon carbide, one or more metallic carbides, one or more transition metal nitrides, one or more metallic phosphides, one or more carbon-containing particles, one or more superionic conductors, one or more phosphate electrolytes, one or more mixed oxides being doped with one or more lower-valent cations and/or one or more and/or mixed sulphides being doped with one or more lower-valent cations and/or any mixture thereof; with preference in a content of from 50 wt. % to 100 wt. % based on the total weight of the electrically conductive particles of the bed; preferably, from 60 wt. % to 100 wt. %; more preferably from 70 wt. % to 100 wt. %; even more preferably from 80 wt. % to 100 wt. % and most preferably from 90 wt. % to 100 wt. %.

For example, the electrically conductive particles of the bed are or comprise one or more selected from one or more metallic alloys, one or more non-metallic resistors, one or more carbon-containing particles, one or more mixed oxides being doped with one or more lower-valent cations, one or more mixed sulphides being doped with one or more lower-valent cations, and/or any mixture thereof; with preference in a content of from 50 wt. % to 100 wt. % based on the total weight of the electrically conductive particles of the bed; preferably, from 60 wt. % to 100 wt. %; more preferably from 70 wt. % to 100 wt. %; even more preferably from 80 wt. % to 100 wt. % and most preferably from 90 wt. % to 100 wt. %.

For example, the electrically conductive particles of the bed are or comprise one or more carbon-containing particles and one or more selected from one or more metallic alloys, one or more non-metallic resistors, one or more mixed oxides being doped with one or more lower-valent cations, one or more mixed sulphides being doped with one or more lower-valent cations, and/or any mixture thereof with preference in a content of from 50 wt. % to 100 wt. % based on the total weight of the electrically conductive particles of the bed; preferably, from 60 wt. % to 100 wt. %; more preferably from 70 wt. % to 100 wt. %; even more preferably from 80 wt. % to 100 wt. % and most preferably from 90 wt. % to 100 wt. %.

For example, the electrically conductive particles of the bed are or comprise one or more selected from one or more metallic alloys, one or more non-metallic resistors, one or more mixed oxides being doped with one or more lower-valent cations, one or more mixed sulphides being doped with one or more lower-valent cations, and/or any mixture thereof; with preference in a content of from 50 wt. % to 100 wt. % based on the total weight of the electrically conductive particles of the bed; preferably, from 60 wt. % to 100 wt. %; more preferably from 70 wt. % to 100 wt. %; even more preferably from 80 wt. % to 100 wt. % and most preferably from 90 wt. % to 100 wt. %.

For example, the electrically conductive particles of the bed are or comprise one or more selected from one or more non-metallic resistors, one or more carbon-containing particles, one or more superionic conductors, one or more phosphate electrolytes, one or more mixed oxides being doped with one or more lower-valent cations, one or more mixed sulphides being doped with one or more lower-valent cations, and/or any mixture thereof; with preference in a content of from 50 wt. % to 100 wt. % based on the total weight of the electrically conductive particles of the bed; preferably, from 60 wt. % to 100 wt. %; more preferably from 70 wt. % to 100 wt. %; even more preferably from 80 wt. % to 100 wt. % and most preferably from 90 wt. % to 100 wt. %.

For example, the electrically conductive particles of the bed are or comprise one or more selected from one or more metallic alloys, one or more non-metallic resistors, one or more metallic carbides, one or more transition metal nitrides, one or more metallic phosphides, one or more superionic conductors, one or more phosphate electrolytes, one or more mixed oxides being doped with one or more lower-valent cations, one or more mixed sulphides being doped with one or more lower-valent cations, and/or any mixture thereof; with preference in a content of from 50 wt. % to 100 wt. % based on the total weight of the electrically conductive particles of the bed; preferably, from 60 wt. % to 100 wt. %; more preferably from 70 wt. % to 100 wt. %; even more preferably from 80 wt. % to 100 wt. % and most preferably from 90 wt. % to 100 wt. %.

For example, said one or more metallic alloys particles are selected from Ni—Cr, Fe—Ni—Cr, Fe—Ni—Al or a mixture thereof. With preference, when said metallic alloy comprises at least chromium, the chromium content is at least 15 mol. % of the total molar content of said metallic alloy comprising at least chromium, more preferably at least 20 mol. %, even more preferably at least 25 mol. %, most preferably at least 30 mol. %. Advantageously yet, the iron content in the metallic alloys is at most 2.0% based on the total molar content of said metallic alloy, preferably at most 1.5 mol. %, more preferably at most 1.0 mol. %, even more preferably at most 0.5 mol. %.

For example, non-metallic resistors particles are selected from silicon carbide (SiC), molybdenum disilicide ($MoSi_2$), nickel silicide (NiSi), sodium silicide ($Na_2Si$), magnesium silicide ($Mg_2Si$), platinum silicide (PtSi), titanium silicide ($TiSi_2$), tungsten silicide ($WSi_2$) or a mixture thereof; preferably non-metallic resistors particles are silicon carbide. In an alternative, said non-metallic resistors particles are selected from molybdenum disilicide ($MoSi_2$), nickel silicide (NiSi), sodium silicide ($Na_2Si$), magnesium silicide ($Mg_2Si$), platinum silicide (PtSi), titanium silicide ($TiSi_2$), tungsten silicide ($WSi_2$) or a mixture thereof.

For example, said one or more metallic carbides are selected from iron carbide ($Fe_3C$), molybdenum carbide (such as a mixture of MoC and $Mo_2C$).

For example, said one or more transition metal nitrides are selected from zirconium nitride (ZrN), tungsten nitride (such as a mixture of $W_2N$, WN, and $WN_2$), vanadium nitride (VN), tantalum nitride (TaN), and/or niobium nitride (NbN).

For example, said one or more metallic phosphides are selected from copper phosphide ($Cu_3P$), indium phosphide (InP), gallium phosphide (GaP), sodium phosphide $Na_3P$), aluminium phosphide (AlP), zinc phosphide ($Zn_3P_2$) and/or calcium phosphide ($Ca_3P_2$).

For example, said one or more carbon-containing particles are selected from graphite, petroleum coke, carbon black, coke or a mixture thereof, preferably from graphite and/or carbon black.

For example, said one or more mixed oxides particles are ionic or mixed conductors being doped with one or more lower-valent cations. Advantageously, said mixed oxides are doped with one or more lower-valent cations, and are selected from oxides having a cubic fluorite structure, perovskite, and/or pyrochlore.

For example, said one or more mixed sulphides are ionic or mixed conductors being doped with one or more lower-valent cations.

For example, the electrically conductive particles of the bed are or comprise silicon carbide. For example, the silicon carbide is selected from sintered silicon carbide, nitride-bounded silicon carbide, recrystallised silicon carbide, reaction bonded silicon carbide and any mixture thereof. The type of silicon carbide material is selected according to the required heating power necessary for supplying the reaction heat of the endothermic dehydrogenation and/or aromatization of hydrocarbons reaction.

For example, the electrically conductive particles of the bed are or comprise a mixture of a non-metallic resistor being silicon carbide and electrically conductive particles different from said silicon carbide. The presence of electrically conductive particles different from said silicon carbide in the bed is optional. It can be present as a starting material for heating the bed since it was found that the resistivity of silicon carbide at room temperature is too high to start heating the bed. Alternatively to the presence of electrically conductive particles different from silicon carbide, it is possible to provide heat to the reactor for a defined time to start the reaction.

For example, the electrically conductive particles of the bed are or comprise a mixture of a non-metallic resistor being silicon carbide and electrically conductive particles different from said silicon carbide and the electrically conductive particles of the bed comprises from 10 wt. % to 99 wt. % of silicon carbide based on the total weight of the particles of the bed; preferably, from 15 wt. % to 95 wt. %, more preferably from 20 wt. % to 90 wt. %, even more preferably from 25 wt. % to 80 wt. % and most preferably from 30 wt. % to 75 wt. %.

For example, the electrically conductive particles of the bed are or comprise a mixture of a non-metallic resistor being silicon carbide and electrically conductive particles different from said silicon carbide and the electrically conductive particles different from silicon carbide are one or more carbon-containing particles and/or one or more mixed oxides being doped with one or more lower-valent cations, and/or one or more mixed sulphides being doped with one or more lower-valent cations; with preference, the carbon-containing particles are selected from graphite, carbon black, coke, petroleum coke and/or any mixture thereof.

For example, the electrically conductive particles of the bed are or comprise one or more mixed oxides being ionic conductor, namely being doped with one or more lower-valent cations; with preference, the mixed oxides being doped with one or more lower-valent cations are selected from:
- one or more oxides having a cubic fluorite structure being at least partially substituted with one or more lower-valent cations; preferably selected from Sm, Gd, Y, Sc, Yb, Mg, Ca, La, Dy, Er, Eu; and/or
- one or more $ABO_3$-perovskites with A and B tri-valent cations being at least partially substituted in A position with one or more lower-valent cations, preferably selected from Ca, Sr, or Mg, and comprising at least one of Ni, Ga, Co, Cr, Mn, Sc, Fe and/or a mixture thereof in B position; and/or
- one or more $ABO_3$-perovskites with A bi-valent cation and B tetra-valent cation, being at least partially substituted with one or more lower-valent cations, preferably selected from Mg, Sc, Y, Nd or Yb in the B position or with a mixture of different B elements in the B position; and/or
- one or more $A_2B_2O_7$-pyrochlores with A tri-valent cation and B tetra-valent cation, being at least partially substituted in A position with one or more lower-valent cations, preferably selected from Ca or Mg, and comprising at least one of Sn, Zr and Ti in B position.

Examples of one or more mixed sulphides are
- one or more sulphides having a cubic fluorite structure being at least partially substituted with one or more lower-valent cations, preferentially selected from Sm, Gd, Y, Sc, Yb, Mg, Ca, La, Dy, Er, Eu; and/or
- one or more $ABS_3$ structures with A and B tri-valent cations being at least partially substituted in A position with one or more lower-valent cations, preferably selected from Ca, Sr, or Mg, and comprising at least one of Ni, Ga, Co, Cr, Mn, Sc, Fe and/or a mixture thereof in B position; and/or
- one or more $ABS_3$ structures with A bi-valent cation and B tetra-valent cation, being at least partially substituted with one or more lower-valent cations, preferably selected from Mg, Sc, Y, Nd or Yb in the B position or with a mixture of different B elements in the B position; and/or
- one or more $A_2B_2S_7$ structures with A tri-valent cation and B tetra-valent cation, being at least partially substituted in A position with one or more lower-valent cations, preferably selected from Ca or Mg, and comprising at least one of Sn, Zr and Ti in B position.

With preference, the degree of substitution in the one or more mixed oxides doped with one or more lower-valent cations and having a cubic fluorite structure is between 1 and 15 atom % based on the total number of atoms present in the one or more oxides having a cubic fluorite structure, preferably between 3 and 12 atom %, more preferably between 5 and 10 atom %.

With preference, the degree of substitution in the one or more mixed oxides doped with one or more lower-valent cations is between 1 and 50 atom % based on the total number of atoms present in the one or more $ABO_3$-perovskites with A and B tri-valent cations, in the one or more $ABO_3$-perovskites with A bivalent cation and B tetra-valent cation or in the one or more $A_2B_2O_7$-pyrochlores with A trivalent cation and B tetra-valent cation respectively, preferably between 3 and 20 atom %, more preferably between 5 and 15 atom %.

With preference, the degree of substitution in the one or more mixed sulphides doped with one or more lower-valent cations and having a cubic fluorite structure is between 1 and 15 atom % based on the total number of atoms present in the one or more oxides having a cubic fluorite structure, preferably between 3 and 12 atom %, more preferably between 5 and 10 atom %.

With preference, the degree of substitution in the one or more mixed sulphides doped with one or more lower-valent cations is between 1 and 50 atom % based on the total number of atoms present in the one or more $ABS_3$ structures with A and B tri-valent cations, in the one or more $ABS_3$ structures with A bivalent cation and B tetra-valent cation or in the one or more $A_2B_2S_7$ structures with A trivalent cation and B tetra-valent cation respectively, preferably between 3 and 20 atom %, more preferably between 5 and 15 atom %.

For example, the electrically conductive particles of the bed are or comprise one or more metallic alloys; with preference, one or more metallic alloys are selected from Ni—Cr, Fe—Ni—Cr, Fe—Ni—Al or a mixture thereof.

With preference, when said metallic alloy comprises at least chromium, the chromium content is at least 15 mol. % of the total molar content of said metallic alloy comprising at least chromium, more preferably at least 20 mol. %, even more preferably at least 25 mol. %, most preferably at least 30 mol. %. Advantageously yet, the iron content in the metallic alloys is at most 2.0% based on the total molar content of said metallic alloy, preferably at most 1.5 mol. %, more preferably at most 1.0 mol. %, even more preferably at most 0.5 mol. %.

In the case where said electrically conductive particles different from said silicon carbide particles are particles are selected from non-metallic resistors, said non-metallic resistor is preferably molybdenum disilicide ($MoSi_2$).

In the case where said electrically conductive particles are different from said silicon carbide particles are particles are selected from carbon-containing particles, said carbon-containing particle is preferably one or more selected from graphite, petroleum coke, coke and/or carbon black. For example, the electrically conductive particles of the bed are or comprise a mixture of silicon carbide particles and electrically conductive particles different from said silicon carbide wherein the electrically conductive particles different from said silicon carbide particles is or comprises graphite particles and one or more wherein the graphite particles have an average particle size ranging from 5 to 300 μm as determined by sieving according to ASTM D4513-11, more preferably ranging from 10 to 200 μm and most preferably ranging from 20 to 200 μm or from 30 to 150 μm.

The Particles of a Catalytic Composition

For example, the content of the particles of a catalytic composition based on the total weight of the particles of the bed is ranging from 30 wt. % to 100 wt. %; preferably from 32 wt. % to 95 wt. %, more preferably from 35 wt. % to 90 wt. %, even more preferably from 37 wt. % to 85 wt. %, most preferably from 40 wt. % to 80 wt. %, even most preferably from 45 wt. % to 75 wt. % or from 50 wt. % to 70 wt. %. In the case where the content of the particles of a catalytic composition based on the total weight of the particles of the bed is 100 wt. %, said particles of a catalytic composition are also electrically conductive particles.

For example, the particles of a catalytic composition have an average particle size ranging from 5 to 300 μm as determined by sieving according to ASTM D4513-11, preferably ranging from 10 to 200 μm and more preferably ranging from 20 to 200 μm or from 30 to 150 μm.

Determination by sieving according to ASTM D4513-11 is preferred. In case the particles have an average size of below 20 μm the determination of the average size can also be done by Laser Light Scattering according to ASTM D4464-15.

The catalytic composition comprises one or more metallic compounds. In an embodiment, the catalytic composition comprises:
one or more catalyst materials selected from gallium, zinc, chromium, iron, metal of the group VIII or mixtures thereof, and one or more catalytic supports; or
from 50 to 85 wt. % of $Fe_2O_3$ based on the total weight of the catalyst composition; from 3 to 25 wt. % of $K_2O$; from 3 to 30 wt. % of $CeO_2$; from 0.1 to 5 wt. % of CaO; from 0.1 to 5 wt. % of $Na_2O$ and from 0.1 to 150 ppm of at least one element selected from Pb, Pt, Os, Ir, Ru, Re, Pd, Ag, Au, Sn or any mixture thereof; or
from 0.01 to 3.0 wt. % of one or more metals of the group VIII based on the total weight of the catalyst composition, from 0.1 to 3.5 wt. % of a halide; and from 0.01 to 5.0 wt. % of one or more metals selected from groups IIIA, IVA, IB, VIB and/or VIIB; or
from 5.0 to 90.0 wt. % of one or more zeolites comprising at least one 10-membered ring channel and based on the total weight of the catalyst composition, from 0.1 to 5.0 wt. % of a halide; and from 0.05 to 10.0 wt. % of one or more catalyst materials selected from Ga, In, Zn, Cu, Re, Mo, W; or from 0.005 to 1.0 wt. % of one or more metals of the group VIII or mixtures thereof based on the total weight of the catalyst composition.

In an embodiment, the process is selected from a paraffin dehydrogenation process, an alkyl-aromatic dehydrogenation process, a naphtha reforming process and a paraffin aromatisation process.

For example, the process is a paraffin dehydrogenation process. In this case, the catalytic composition comprises one or more catalyst materials selected from gallium, zinc, chromium, iron, metal of the group VIII or mixtures thereof; and one or more catalytic supports preferably selected from one or more refractory materials. With preference, said one or more refractory materials are one or more selected from $Al_2O_3$, $TiO_2$, $ZrO_2$, $HfO_2$, $La_2O_3$, MgO, $CeO_2$, $ZrO_2/MgO$, $ZrO_2/La_2O_3$, $ZrO_2/Y_2O_3$, $ZrO_2/CeO_2$.

For example, the process is an alkyl-aromatic dehydrogenation process. In this case, the catalyst composition comprises
from 50 to 85 wt. % of $Fe_2O_3$ based on the total weight of the catalyst composition, preferably from 55 to 83 wt. %, more preferably from 60 to 80 wt. %;
from 3 to 25 wt. % of $K_2O$ based on the total weight of the catalyst composition; preferably from 3.5 to 22 wt. %, more preferably from 4 to 20 wt. %;
from 3 to 30 wt. % of $CeO_2$ based on the total weight of the catalyst composition, preferably from 4 to 27 wt. %, more preferably from 5 to 25 wt. %;

from 0.1 to 5 wt. % of CaO based on the total weight of the catalyst composition, preferably from 0.3 to 4.5 wt. %, more preferably from 0.5 to 4.0 wt. %;

from 0.1 to 5 wt. % of $Na_2O$ based on the total weight of the catalyst composition, preferably from 0.3 to 4.5 wt. %, more preferably from 0.5 to 4.0 wt. %; and from 0.1 to 150 ppm of at least one element selected from Pb, Pt, Os, Ir, Ru, Re, Pd, Ag, Au, Sn or any mixture thereof;

optionally from 0.001 to 5.0 wt. % of at least one oxide based on the total weight of the catalyst composition, preferably from 0.01 to 4.5 wt. %, more preferably from 0.1 to 4.0 wt. %; said at least one oxide being selected from the group comprising Mg, Ti, Zr, V, Nb, Cr, W, Co, Ni, Cu, Zn, B, Al, Ga, In, Si, Ge, Sn, P, Sb, Bi, Y, La, Pr, Nd, Dy and Sm;

optionally from 0.1 to 5.0 wt. % of $MnO_2$ based on the total weight of the catalyst composition, preferably from 0.3 to 4.5 wt. %, more preferably from 0.5 to 4.0 wt. %;

optionally from 0.1 to 4.0 wt. % of solid carbon based on the total weight of the catalyst composition, preferably from 0.3 to 3.5 wt. %, more preferably from 0.5 to 3.0 wt. %; with preference, said solid carbon is one or more selected from graphite, carbon black, petcoke and/or graphene.

For example, the process is a naphtha reforming process. In this case, the catalyst composition comprises from 0.01 to 3.0 wt. % of one or more metals of the group VIII based on the total weight of the catalyst composition, preferably from 0.05 to 2.5 wt. %, more preferably from 0.1 to 1.0 wt. %; with preference, said one or more metals of the group VIII are Pd, Pt, Ir, Rh, Os, and/or Ru, more preferably Pt;

from 0.1 to 3.5 wt. % of a halogen based on the total weight of the catalyst composition, preferably from 0.3 to 2.0 wt. %, more preferably from 0.5 to 1.5 wt. %; with preference said halogen is F, Cl, I and/or Br, more preferably Cl; and from 0.01 to 5.0 wt. % of one or more metals selected from groups IIIA, IVA, IB, VIB and/or VIIB based on the total weight of the catalyst composition, preferably from 0.05 to 4.0 wt. %, more preferably from 0.1 to 3.0 wt. %; with preference said one or more metals are Re and/or Sn;

optionally from 0.1 to 4.0 wt. % of solid carbon based on the total weight of the catalyst composition, preferably from 0.3 to 3.5 wt. %, more preferably from 0.5 to 3.0 wt. %; with preference, said solid carbon is one or more selected from graphite, carbon black, petcoke and/or graphene;

optionally from 1.0 to 30.0 wt. % of one or more zeolites based on the total weight of the catalyst composition, preferably from 1.5 to 25.0 wt. %, more preferably from 2.0 to 20.0 wt. %; with preference, said one or more zeolites comprises 10- to 12-member ring.

For example, the process is a paraffin aromatisation process. In this case, the catalyst composition comprises from 5.0 to 90.0 wt. % of one or more zeolites comprising at least one 10-membered ring channel and based on the total weight of the catalyst composition, preferably from 10.0 to 85.0 wt. %, more preferably from 20.0 to 80.0 wt. % and/or from 5.0 to 90.0 wt. % of one or more zeolites comprising pores with a diameter of at least 0.5 nm as determined by argon adsorption and based on the total weight of the catalyst composition, preferably from 10.0 to 85.0 wt. %, more preferably from 20.0 to 80.0 wt. %. With preference, said one or more zeolites comprise between at least one 10-membered ring channel and at least one 12-membered ring channel and/or comprise pore with a diameter between 0.5 nm and 1.5 nm, preferably between 0.7 nm and 0.9 nm.

from 0.1 to 5.0 wt. % of a halide based on the total weight of the catalyst composition, preferably from 0.2 to 3.5 wt. %, more preferably from 0.3 to 3.0 wt. %; with preference said halogen is F, Cl, I and/or Br, more preferably Cl; and from 0.05 to 10.0 wt. % of one or more catalyst materials selected from Ga, In, Zn, Cu, Re, Mo, W, or from 0.005 to 1.0 wt. % of one or more metals of the group VIII or mixtures thereof based on the total weight of the catalyst composition, preferably from 0.01 to 0.7 wt. %, more preferably from 0.05 to 0.5 wt. %. With preference, said one or more metals of the group VIII are one or more of Pt, Pd, Rh, Ir, Ru, Os, more preferably Pt;

optionally, from 0.1 to 15.0 wt. % of a rare earth element based on the total weight of the catalyst composition.

The Process

For example, the step of heating the fluidized bed is performed by passing an electric current at a voltage of at most 300 V through the fluidized bed, preferably at most 200 V, more preferably at most 150 V, even more preferably at most 120 V, most preferably at most 100 V, even most preferably at most 90 V.

For example, said process comprises a step of pre-heating with a gaseous stream said fluidized bed reactor before conducting said endothermic dehydrogenation and/or aromatisation reaction in the fluidized bed reactor; with preference, said gaseous stream is a stream of inert gas and/or has a temperature comprised between 480° C. and 700° C.

For example, wherein the at least one fluidized bed reactor provided in step a) comprises a heating zone and a reaction zone and wherein the fluid stream provided in step b) is provided to the heating zone and comprises diluent gases, the step c) of heating the fluidized bed to a temperature ranging from 480° C. to 700° C. to conduct said endothermic dehydrogenation and/or aromatisation reaction comprises the following sub steps:

heating the fluidized bed to a temperature ranging from 480° C. to 700° C. by passing an electric current through the heating zone of the at least one fluidized bed, transporting the heated particles from the heating zone to the reaction zone, in the reaction zone, putting the heated particles in a fluidized state by passing upwardly through the said bed of the reaction zone a fluid stream comprising one or more hydrocarbons and optional diluent gases to obtain a fluidized bed and to conduct said endothermic dehydrogenation and/or aromatisation reaction, optionally, recovering the particles from the reaction zone and recycling them to the heating zone.

Step c) provides that the endothermic dehydrogenation and/or aromatisation reaction is performed on one or more hydrocarbons, which implies that one or more hydrocarbons are provided.

For example, wherein the heating zone and the reaction zone are mixed (i.e. the same zone); the fluid stream provided in step b) comprises one or more hydrocarbons. The fluid stream may be a vaporized stream.

For example, wherein the heating zone and the reaction zone are separated zones, the fluid stream provided in step b) to the heating zone is devoid of hydrocarbons. For example, wherein the process comprises providing at least one fluidized bed reactor being a heating zone and at least one fluidized bed reactor is a reaction zone, the fluid stream provided in step b) to the heating zone is devoid of hydrocarbons and the fluid stream provided in step b) to the reaction zone comprises one or more hydrocarbons.

It is understood that the one or more hydrocarbons are provided to the reaction zone and that when the heating zone is separated from the reaction zone, no hydrocarbon is provided to the heating zone.

The Installation

According to a second aspect, the disclosure provides for an installation for a process to perform an endothermic dehydrogenation and/or aromatisation reaction, according to the first aspect, said installation comprising a vaporizer and at least one fluidized bed reactor arranged downstream the vaporizer, wherein the at least one fluidized bed reactor comprises:

at least two electrodes; with preference, one electrode is a submerged central electrode or two electrodes are submerged electrodes;
a reactor vessel;
one or more fluid nozzles for the introduction of a fluidizing gas and/or of a reaction fluid within the reactor; and
a bed comprising particles;

the installation is remarkable in that the particles of the bed comprise electrically conductive particles and particles of a catalytic composition, wherein at least 10 wt. % of the particles based on the total weight of the particles of the bed are electrically conductive particles and have a resistivity ranging from 0.001 Ohm·cm to 500 Ohm·cm at 500° C. wherein the catalytic composition comprises one or more metallic compounds.

For example, the electrically conductive particles of the bed are or comprise one or more particles selected from one or more metallic alloys, one or more non-metallic resistors, one or more metallic carbides, one or more transition metal nitrides, one or more metallic phosphides, one or more carbon-containing particles, one or more superionic conductors, one or more phosphate electrolytes, one or more mixed oxides being doped with one or more lower-valent cations, one or more mixed sulphides being doped with one or more lower-valent cations, and any mixture thereof.

In an embodiment, from 50 wt. % to 100 wt. % of the electrically conductive particles of the bed based on the total weight of the electrically conductive particles of the bed are one or more particles selected from one or more metallic alloys, one or more non-metallic resistors, one or more metallic carbides, one or more transition metal nitrides, one or more metallic phosphides, one or more carbon-containing particles, one or more superionic conductors, one or more phosphate electrolytes, one or more mixed oxides being doped with one or more lower-valent cations, one or more mixed sulphides being doped with one or more lower-valent cations, and any mixture thereof; preferably, from 60 wt. % to 100 wt. %; more preferably from 70 wt. % to 100 wt. %; even more preferably from 80 wt. % to 100 wt. % and most preferably from 90 wt. % to 100 wt. %.

With preference, the catalytic composition comprises:
one or more catalyst materials selected from gallium, zinc, chromium, iron, metal of the group VIII or mixtures thereof, and one or more catalytic supports; or
from 50 to 85 wt. % of $Fe_2O_3$ based on the total weight of the catalyst composition; from 3 to 25 wt. % of $K_2O$; from 3 to 30 wt. % of $CeO_2$; from 0.1 to 5 wt. % of CaO; from 0.1 to 5 wt. % of $Na_2O$ and from 0.1 to 150 ppm of at least one element selected from Pb, Pt, Os, Ir, Ru, Re, Pd, Ag, Au, Sn or any mixture thereof; or
from 0.01 to 3.0 wt. % of one or more metals of the group VIII based on the total weight of the catalyst composition, from 0.1 to 3.5 wt. % of a halide; and from 0.01 to 5.0 wt. % of one or more metals selected from groups IIIA, IVA, IB, VIB and/or VIIB; or
from 5.0 to 90.0 wt. % of one or more zeolites comprising at least one 10-membered ring channel and based on the total weight of the catalyst composition, from 0.1 to 5.0 wt. % of a halide; and from 0.05 to 10.0 wt. % of one or more catalyst materials selected from Ga, In, Zn, Cu, Re, Mo, W; or from 0.005 to 1.0 wt. % of one or more metals of the group VIII or mixtures thereof based on the total weight of the catalyst composition 10-membered ring channel and based on the total weight of the catalyst composition.

With preference, the process is selected from a paraffin dehydrogenation process, an alkyl-aromatic dehydrogenation process, a naphtha reforming process and a paraffin aromatisation process.

The reaction fluid comprises one or more hydrocarbons.

With preference, the installation further comprises a desulfurization reactor arranged upstream the at least one fluidized bed reactor, more preferably between the vaporizer and the at least one fluidized bed reactor.

Advantageously, at least one fluidized bed reactor is devoid of heating means. For example, at least one fluidized bed reactor comprises a reactor vessel and is devoid of heating means located around or inside the reactor vessel. For example, all the fluidized bed reactors are devoid of heating means. When stating that at least one of the fluidized bed reactor is devoid of "heating means", it refers to "classical" heating means, such as ovens, gas burners, hot plates and the like. There are no other heating means than the at least two electrodes of the fluidized bed reactor itself. For example, at least one fluidized bed reactor is devoid of heating means selected from ovens, gas burners, hot plates, or any combination thereof. For example, all the fluidized bed reactors are devoid of heating means selected from ovens, gas burners, hot plates, or any combination thereof.

In a preferred embodiment, the at least one fluidized bed reactor comprising at least two electrodes and a bed comprising particles is devoid of packing.

For example, the at least one reactor vessel has an inner diameter of at least 100 cm, preferably at least 200 cm, more preferably at least 300 cm.

With preference, the reactor vessel comprises a reactor wall made of materials that are corrosion-resistant materials and advantageously said reactor wall materials comprise nickel (Ni), SiAlON ceramics, yttria-stabilized zirconia (YSZ), tetragonal polycrystalline zirconia (TZP) and/or tetragonal zirconia polycrystal (TPZ).

With preference, one of the electrodes is the reactor vessel or the gas distributor and/or said at least two electrodes are made in stainless steel material or nickel-chromium alloys or nickel-chromium-iron alloys.

For example, the process is according to the first aspect.

For example, the at least one fluidized bed reactor comprises a heating zone and a reaction zone, one or more fluid nozzles to provide the reaction fluid to the reaction zone, and means to transport the particles from the heating zone to the reaction zone and optional means to transport the particles from the reaction zone back to the heating zone. This configuration is remarkable in that a given particle bed is common to said at least one fluidized bed reactor. A common bed particle can thus be distributed between at least two fluidized bed reactors and be continuously moved from one reactor to another one.

For example, the installation comprises at least two fluidized bed reactors connected one to each other wherein at least one of said at least two fluidized bed reactors is the heating zone and at least another of said at least two fluidized bed reactors is the reaction zone. With preference, the installation comprises one or more fluid nozzles arranged to the reaction fluid to the at least one fluidized bed reactor being the reaction zone.

For example, the at least one fluidized bed reactor is a single fluidized bed reactor wherein the heating zone is the bottom part of the fluidized bed reactor while the reaction zone is the top part of the fluidised bed reactor. With preference, the installation comprises one or more fluid nozzles to inject the reaction fluid between the two zones. The diameter of the heating zone and reaction zone can be different to accomplish optimum conditions for heating in the bottom zone and optimum conditions for hydrocarbon conversion in the top zone. Particles can move from the heating zone to the reaction zone by entrainment and the other way around from the reaction zone back to the heating zone by gravity. Optionally, particles can be collected from the upper heating zone and transferred by a separate transfer line back to the bottom heating zone.

For example, the at least one fluidized bed comprises at least two lateral zones being an outer zone and an inner zone wherein the outer zone is surrounding the inner zone, with the outer zone being the heating zone and the inner zone being the reaction zone. In a less preferred configuration, the outer zone is the reaction zone and the inner zone is the heating zone. With preference, the installation comprises one or more fluid nozzles to inject a hydrocarbon feedstock in the reaction zone.

The Use of a Particle Bed

According to a third aspect, the disclosure provides for the use of a bed comprising particles in at least one fluidized bed reactor to perform a process of dehydrogenation and/or aromatisation of hydrocarbons according to the first aspect, the use is remarkable in that the particles of the bed comprise electrically conductive particles and particles of a catalytic composition, wherein at least 10 wt. % of the particles based on the total weight of the particles of the bed are electrically conductive particles and have a resistivity ranging from 0.001 Ohm·cm to 500 Ohm·cm at 500° C. wherein the catalytic composition comprises one or more metallic compounds.

For example, the use comprises heating the bed comprising particles to a temperature ranging from 480° C. to 700° C. in a first reactor, transporting the heated particle bed from the first reactor to a second reactor and providing one or more hydrocarbons to the second reactor; with preference, at least the second reactor is a fluidized bed reactor and/or at least the second reactor is devoid of heating means; more preferably, the first reactor and the second reactor are fluidized bed reactors and/or the first and the second reactor are devoid of heating means.

For example, the electrically conductive particles of the bed are or comprise one or more particles selected from one or more metallic alloys, one or more non-metallic resistors, one or more metallic carbides, one or more transition metal nitrides, one or more metallic phosphides, one or more carbon-containing particles, one or more superionic conductors, one or more phosphate electrolytes, one or more mixed oxides being doped with one or more lower-valent cations, one or more mixed sulphides being doped with one or more lower-valent cations, and any mixture thereof.

In an embodiment, from 50 wt. % to 100 wt. % of the electrically conductive particles of the bed based on the total weight of the electrically conductive particles of the bed are one or more particles selected from one or more metallic alloys, one or more non-metallic resistors, one or more metallic carbides, one or more transition metal nitrides, one or more metallic phosphides, one or more carbon-containing particles, one or more superionic conductors, one or more phosphate electrolytes, one or more mixed oxides being doped with one or more lower-valent cations, one or more mixed sulphides being doped with one or more lower-valent cations, and any mixture thereof; preferably, from 60 wt. % to 100 wt. %; more preferably from 70 wt. % to 100 wt. %; even more preferably from 80 wt. % to 100 wt. % and most preferably from 90 wt. % to 100 wt. %.

According to a fourth aspect, the disclosure provides the use of an installation comprising at least one fluidized bed reactor to perform a dehydrogenation and/or aromatisation of hydrocarbons, remarkable in that the installation is according to the second aspect. With preference, the use of an installation with at least one fluidized bed reactor to perform a dehydrogenation and/or aromatisation of hydrocarbons in a process according to the first aspect.

The particular features, structures, characteristics or embodiments may be combined in any suitable manner, as would be apparent to a person skilled in the art from this disclosure, in one or more embodiments.

DETAILED DESCRIPTION

Figure 1:
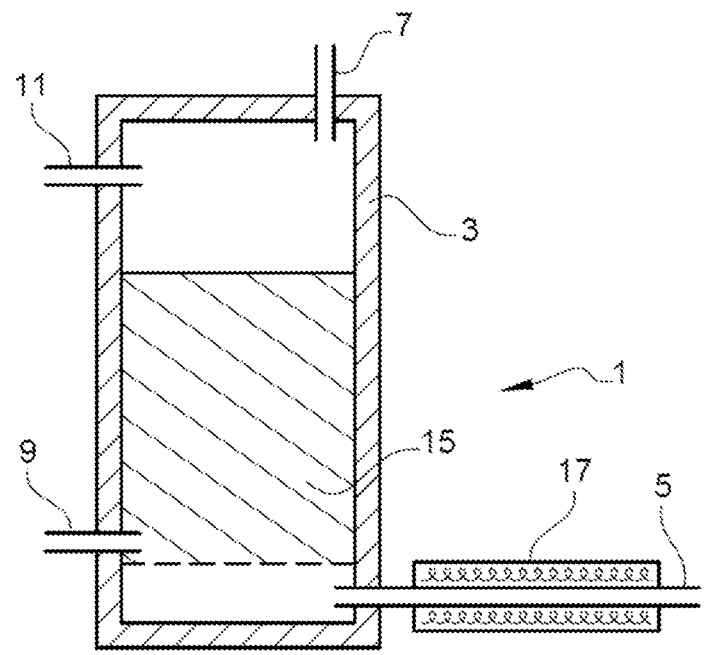
FIG. 1 illustrates an installation according to the prior art.

For the disclosure, the following definitions are given:

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The recitation of numerical ranges by endpoints includes all integer numbers and, where appropriate, fractions subsumed within that range (e.g., 1 to 5 can include 1, 2, 3, 4, 5 when referring to, for example, a number of elements, and can also include 1.5, 2, 2.75 and 3.80, when referring to, for example, measurements). The recitation of endpoints also includes the recited endpoint values themselves (e.g., from 1.0 to 5.0 includes both 1.0 and 5.0). Any numerical range recited herein is intended to include all sub-ranges subsumed therein.

Zeolite codes (e.g., CHA . . . ) are defined according to the "*Atlas of Zeolite Framework Types*", 6th revised edition, 2007, Elsevier, to which the present application also refers.

The present disclosure provides for a process to perform a dehydrogenation and/or aromatisation of hydrocarbons having at least two carbons to produce olefins and/or aromatics, said process comprising the steps of:

a) providing at least one fluidized bed reactor comprising at least two electrodes and a bed comprising particles;
b) putting the particles of the bed in a fluidized state by passing upwardly through the said bed a fluid stream to obtain a fluidized bed;
c) heating the fluidized bed to a temperature ranging from 480° C. to 700° C. to conduct the endothermic dehydrogenation and/or aromatisation reaction; and
d) obtaining a reactor effluent containing hydrogen, unconverted hydrocarbons, and olefins and/or aromatics;

the process is remarkable in that the particles of the bed comprise electrically conductive particles and particles of a catalytic composition, wherein at least 10 wt. % of the particles based on the total weight of the particles of the bed are electrically conductive particles and have a resistivity ranging from 0.001 Ohm·cm to 500 Ohm·cm at 500° C. wherein the catalytic composition comprises one or more metallic compounds and in that the step (c) of heating the fluidized bed is performed by passing an electric current through the fluidized bed.

In a preferred embodiment, the at least one fluidized bed reactor comprising at least two electrodes and a bed comprising particles is devoid of packing.

With preference, the catalytic composition comprises:
one or more catalyst materials selected from gallium, zinc, chromium, iron, metal of the group VIII or mixtures thereof, and one or more catalytic supports; or
from 50 to 85 wt. % of $Fe_2O_3$ based on the total weight of the catalyst composition; from 3 to 25 wt. % of $K_2O$; from 3 to 30 wt. % of $CeO_2$; from 0.1 to 5 wt. % of CaO; from 0.1 to 5 wt. % of $Na_2O$ and from 0.1 to 150 ppm of at least one element selected from Pb, Pt, Os, Ir, Ru, Re, Pd, Ag, Au, Sn or any mixture thereof; or
from 0.01 to 3.0 wt. % of one or more metals of the group VIII based on the total weight of the catalyst composition, from 0.1 to 3.5 wt. % of a halide; and from 0.01 to 5.0 wt. % of one or more metals selected from groups IIIA, IVA, IB, VIB and/or VIIB; or
from 5.0 to 90.0 wt. % of one or more zeolites comprising at least one 10-membered ring channel and based on the total weight of the catalyst composition, from 0.1 to 5.0 wt. % of a halide; and from 0.05 to 10.0 wt. % of one or more catalyst materials selected from Ga, In, Zn, Cu, Re, Mo, W; or from 0.005 to 1.0 wt. % of one or more metals of the group VIII or mixtures thereof based on the total weight of the catalyst composition.

For example, the step of heating the fluidized bed is performed by passing an electric current at a voltage of at most 300 V through the fluidized bed, preferably at most 200 V, more preferably at most 150 V, even more preferably at most 120 V, most preferably at most 100 V, even most preferably at most 90 V.

The solid particulate material in the fluidized bed reactor is typically supported by a porous plate, a perforated plate, a plate with nozzles or chimneys, known as a distributor. The fluid is then forced through the distributor up and travelling through the voids between the solid particulate material. At lower fluid velocities, the solids remain settled as the fluid passes through the voids in the material, known as a packed bed reactor. As the fluid velocity is increased, the particulate solids will reach a stage where the force of the fluid on the solids is enough to counterbalance the weight of the solid particulate material. This stage is known as incipient fluidization and occurs at this minimum fluidization velocity. Once this minimum velocity is surpassed, the contents of the reactor bed begin to expand and become fluidized.

Depending on the operating conditions and properties of the solid phase various flow regimes can be observed in such reactors. The minimum fluidization velocity needed to achieve bed expansion depends upon the size, shape, porosity and density of the particles and the density and viscosity of the upflowing fluid. (P. R. Gunjal, V. V. Ranade, in Industrial Catalytic Processes for Fine and Specialty Chemicals, 2016).

Four different categories of fluidization based on the mean particle have been differentiated by Geldart that determine the fluidization regimes:

type A, aeratable fluidization (medium size, medium density particles which are easier to fluidize; Particles of typically 30-100 μm, density~1500 $kg/m^3$);
type B, sand-like fluidization (heavier particles which are difficult to fluidize; Particles of typically 100-800 μm, density between 1500 and 4000 $kg/m^3$);
type C, cohesive fluidization (typical powder-like solid particle fluidization; Fine-size particles (~20 μm) with dominance of intraparticle or cohesive forces); and
type D, spoutable fluidization (large density and larger particle~1-4 mm, dense and spoutable).

Fluidization may be broadly classified into two regimes (Fluid Bed Technology in Materials Processing, 1999 by CRC Press): homogeneous fluidization and heterogeneous fluidization. In homogeneous or particulate fluidization, particles are fluidized uniformly without any distinct voids. In heterogeneous or bubbling fluidization, gas bubbles devoid of solids are distinctly observable. These voids behave like bubbles in gas-liquid flows and exchange gas with the surrounding homogeneous medium with a change in size and shape while rising in the medium. In particulate fluidization, the bed expands smoothly with substantial particle movement and the bed surface is well defined. Particulate fluidization is observed only for Geldart-A type particles. A bubbling fluidization regime is observed at much higher velocities than homogeneous fluidization, in which distinguishable gas bubbles grow from the distributor, may coalesce with other bubbles and eventually burst at the surface of the bed. These bubbles intensify the mixing of solids and gases and bubble sizes tend to increase further with a rise in fluidization velocity. A slugging regime is observed when the bubble diameter increases up to the reactor diameter. In a turbulent regime, bubbles grow and start breaking up with the expansion of the bed. Under these conditions, the top surface of the bed is no longer distinguishable. In fast fluidization or pneumatic fluidization, particles are transported out of the bed and need to be recycled back into the reactor. No distinct bed surface is observed.

Fluidized bed reactors have the following advantages:

Uniform Particle Mixing: Due to the intrinsic fluid-like behavior of the solid particulate material, fluidized beds do not experience poor mixing as in packed beds. The elimination of radial and axial concentration gradients also allows for better fluid-solid contact, which is essential for reaction efficiency and quality.

Uniform Temperature Gradients: Many chemical reactions require the addition or removal of heat. Local hot or cold spots within the reaction bed are avoided in a fluidized situation.

Ability to Operate Reactor Continuously: The fluidized bed nature of these reactors allows for the ability to continuously withdraw the product(s) and introduce new reactants into the reaction vessel. On top of continuous operation of the chemical reactions, the fluidized bed allows also to continuously or at a given frequency withdraw solid material or add continuously or at a given frequency new fresh solid material thanks to the flowable solid particulate material.

Heat can be produced by passing an electrical current through a conducting material that has sufficiently high resistivity (the resistor) to transform electricity into heat. Electrical resistivity (also called specific electrical resistance or volume resistivity, is an intrinsic property independent of shape and size) and its inverse, electrical conductivity, is a fundamental property of a material that quantifies how strongly it resists or conducts electric current (SI unit of electrical resistivity is the ohm-meter ($\Omega \cdot m$) and for conductivity Siemens per meter (S/m)).

When electricity is passed through a fixed bed of electrically conducting particulate solids, having a sufficient resistivity, the bed offers resistance to the flow of current; this resistance depends on many parameters, including the nature of the solid, the nature of the linkages among the particles within the bed, the bed voidage, the bed height, the electrode geometry, etc. If the same fixed bed is fluidized by passing gas, the resistance of the bed increases; the resistance offered by the conducting particles generates heat within the bed and can maintain the bed in isothermal conditions (termed an electrothermal fluidized bed or electrofluid reactor). In many high-temperature reactions, electrofluid reactors offer in situ heating during the reaction and are particularly useful for operating endothermic reactions and hence save energy because no external heating or transfer of heat is required.

It is a prerequisite that at least part of the solid particulate material is electrically conducting but non-conducting solid particulates can be mixed and still result in enough heat generation. Such non-conducting or very high resistivity solids can play a catalytic role in the chemical conversion. The characteristics of the bed material determine the resistance of an electrothermal fluidized bed furnace; as this is a charge resistor type of heat generation, the specific resistivity of the particles affects the bed resistance. The size, shape, composition, and size distribution of the particles also influence the magnitude of the bed resistance. Also, when the bed is fluidized, the voids generated between the particles increases the bed resistance. The total resistance of the bed is the sum of two components, e.g. the electrode contact-resistance (i.e., the resistance between the electrode and the bed) and the bed resistance. A large contact-resistance will cause extensive local heating in the vicinity of the electrode while the rest of the bed stays rather cool.

The following factors determine the contact-resistance: current density, fluidization velocity, type of bed material, electrode size and the type of material used for the electrodes. The electrode compositions can be advantageously metallic like iron, cast iron or other steel alloys, copper or a copper-based alloy, nickel or a nickel-based alloy or refractory like metal, intermetallics or an alloy of Zr, Hf, V, Nb, Ta, Cr, Mo, W or ceramic-like carbides, nitrides or carbon-based like graphite. The area of contact between the bed material and the electrodes can be adjusted, depending on the electrode submergence and the amount of particulate material in the fluidized bed. Hence, the electrical resistance and the power level can be manipulated by adjusting these variables. Advantageously, to prevent overheating of the electrodes compared to the fluidised bed, the resistivity of the electrode should be lower (and hence the joule heating) than of the particulate material of the fluidized bed. In a preferred embodiment, the electrodes can be cooled by passing a colder fluid inside or outside the electrodes. Such fluids can be any liquid that vaporises upon a heating, gas stream or can be a part of the colder feedstock that first cools the electrode before entering the fluidised bed.

Bed resistance can be predicted by the ohmic law. The mechanism of current transfer in fluidized beds is believed to occur through current flow along continuous chains of conducting particles at low operating voltages. At high voltages, a current transfer occurs through a combination of chains of conducting particles and arcing between the electrode and the bed as well as particle-to-particle arcings that might ionize the gas, thereby bringing down the bed resistance. Arcing inside the bed, in principle, is not desirable as it would lower the electrical and thermal efficiency. The gas velocity impacts strongly the bed resistance, a sharp increase in resistance from the settled bed onward when the gas flow rate is increased; a maximum occurred close to the incipient fluidization velocity, followed by a decrease at higher velocities. At gas flow rates sufficient to initiate slugging, the resistance again increased. Particle size and shape impact resistance as they influence the contacts points between particles. In general, the bed resistivity increases 2 to 5 times from a settled bed (e.g. 20 Ohm·cm for graphite) to the incipient fluidisation (60 Ohm·cm for graphite) and 10 to 40 times from a settled bed to twice (300 Ohm·cm for graphite) the incipient fluidisation velocity. Non or less-conducting particles can be added to conducting particles. If the conducting solid fraction is small, the resistivity of the bed would increase due to the breaking of the linkages in the chain of conducting solids between the electrodes. If the non-conducting solid fraction is finer in size, it would fill up the interstitial gaps or voidage of the larger conducting solids and hence increase the resistance of the bed.

In general, for a desired high heating power, a high current at a low voltage is preferred. The power source can be either AC or DC. Voltages applied in an electrothermal fluidized bed are typically below 100 V to reach enough heating power. The electrothermal fluidized bed can be controlled in the following three ways:

1. Adjusting the gas flow: Because the conductivity of the bed depends on the extent of voidage or gas bubbles inside the bed, any variation in the gas flow rate would change the power level; hence the temperature can be controlled by adjusting the fluidizing gas flow rate. The flow rate required for optimum performance corresponds to a velocity which equals or slightly exceeds the minimum fluidization velocity.

2. Adjusting the electrode submergence: The power level can also be controlled by varying the electrode immersion level inside the bed because the conductivity of the bed is dependent on the area of contact between the conducting particles and the electrode: the surface area of the electrode available for current flow increases with electrode submergence, leading to a reduction in overall resistance.

3. Adjusting the applied voltage: although changing the power level by using the first two methods is often more affordable or economical than increasing the applied voltage, however in electrothermal fluidized beds three variables are available to control the produced heating power.

The wall of the reactor is generally made of graphite, ceramics (like SiC), high-melting metals or alloys as it is versatile and compatible with many high-temperature reactions of industrial interest. The atmosphere for the reaction is often restricted to the neutral or the reducing type as an oxidising atmosphere can combust carbon materials or create a non-conducting metal oxide layer on top of metals or alloys. The wall and/or the distribution plate itself can act as an electrode for the reactor. The fluidized solids can be graphite, carbon, or any other high-melting-point, electrically conducting particles. The other electrodes, which is usually immersed in the bed, can also be graphite or a high-melting-point metal, intermetallics or alloys.

It may be advantaged to generate the required reaction heat by heating the conductive particles and/or catalyst particles in a separate zone of the reactor where substantially no hydrocarbons are present, but only diluent gases. The benefit is that the appropriate conditions of fluidization to generate heat by passing an electrical current through a bed of conductive particles can be optimized whereas the optimal reaction conditions during hydrocarbon transformation can be selected for the other zone of the reactor. Such conditions of optimal void fraction and linear velocity might be different for heating purposes and chemical transformation purposes.

In an embodiment of the present disclosure, the installation comprises two zones arranged in series, namely a first zone being a heating zone and a second zone being a reaction zone, where the conductive particles and catalyst particles are continuously moved or transported from the first zone to the second zone and vice versa. The first and second zones can be different parts of a fluidized bed reactor or can be located in separate fluidized bed reactors connected to each other.

In the said embodiment, the process to perform a dehydrogenation and/or aromatisation of hydrocarbons comprises the steps of:
a) providing at least one fluidized bed reactor comprising at least two electrodes and a bed comprising particles;
b) putting the particles of the bed in a fluidized state by passing upwardly through the said bed a fluid stream to obtain a fluidized bed;
c) heating the fluidized bed to a temperature ranging from 480° C. to 700° C. to conduct the endothermic dehydrogenation and/or aromatisation reaction; and
d) obtaining a reactor effluent containing hydrogen, unconverted hydrocarbons, and olefins and/or aromatics;
wherein the particles of the bed comprise electrically conductive particles and particles of a catalytic composition, wherein at least 10 wt. % of the particles based on the total weight of the particles of the bed are electrically conductive particles and have a resistivity ranging from 0.001 Ohm·cm to 500 Ohm·cm at 500° C.
wherein the catalytic composition comprises one or more metallic compounds
wherein the at least one fluidized bed reactor provided in step (a) comprises a heating zone and a reaction zone and wherein the fluid stream provided in step (b) is provided to the heating zone and comprises diluent gases and the step (c) of heating the fluidized bed to a temperature ranging from 480° C. to 700° C. to conduct the endothermic dehydrogenation and/or aromatisation reaction comprises the following sub-steps:
heating the fluidized bed to a temperature ranging from 480° C. to 700° C. by passing an electric current at a voltage of at most 100 V through the heating zone of the at least one fluidized bed;
transporting the heated particles from the heating zone to the reaction zone;
in the reaction zone, putting the heated particles in a fluidized state by passing upwardly through the said bed of the reaction zone a fluid stream comprising one or more hydrocarbons and optional diluent gases to obtain a fluidized bed and to conduct the endothermic dehydrogenation and/or aromatisation reaction;
optionally, recovering the particles from the reaction zone and recycling them to the heating zone.

For example, the diluent gases can be one or more selected from steam, hydrogen, carbon dioxide, methane, ethane, argon, helium, and nitrogen.

For example, the at least one fluidized bed reactor is at least two fluidized bed reactors connected one to each other, wherein at least one of said at least two fluidized bed reactors is the reaction zone. With preference, the at least one fluidized bed reactor being the heating zone comprises gravitational or pneumatic transport means to transport the particles from the heating zone to the reaction zone and/or the installation comprises means arranged to inject one or more hydrocarbons to the at least one fluidized bed reactor being the reaction zone. The installation is devoid of means to inject one or more hydrocarbons to the at least one fluidized bed reactor being the heating zone. For example, the at least one fluidized bed reactor is a single fluidized bed reactor wherein the heating zone is the bottom part of the fluidized bed reactor while the reaction zone is the top part of the fluidised bed reactor. With preference, the installation comprises means to inject one or more hydrocarbons between the two zones.

Step (c) provides that the dehydrogenation and/or aromatisation of hydrocarbons is performed on one or more hydrocarbons which implies that one or more hydrocarbons are provided. It is understood that the one or more hydrocarbons are provided to the reaction zone and that when the heating zone is separated from the reaction zone, then, with preference, no hydrocarbons are provided to the heating zone. It is understood that in addition to the reaction fluid provided to the reaction zone, steam can be provided to the reaction zone. When the heating zone and the reaction zone are mixed (i.e. the same zone); the fluid stream provided in step (b) comprises one or more hydrocarbons.

It is a specific embodiment of the present disclosure that the distance between the heat sources, being the hot particulate material and the feedstock is significantly reduced because of the small size of the particulates and the mixing of the particulates in the vaporous fluidising stream, compared to multitubular catalytic reactors having typically 5 to 25 cm internal diameter or multitubular interheaters or shell-and-tube heat exchanger requiring large temperature gradients to concur the large distance that heat has to travel.

In a preferred embodiment, the volumetric heat generation rate is greater than 0.1 MW/m$^3$ of fluidized bed, more preferably greater than 1 MW/m$^3$, in particular, greater than 3 MW/m$^3$.

The Bed Comprising Particles

According to the disclosure, the particles of the bed comprises electrically conductive particles and catalytic particles. For example, the catalytic particles are electrically conductive. For example, the electrically conductive particles are a mixture of catalytic particles and non-catalytic particles.

To achieve the required temperature necessary to carry out the dehydrogenation and/or aromatisation reaction, at least 10 wt. % of the particles based on the total weight of the particles of the bed are electrically conductive and have a resistivity ranging from 0.001 Ohm·cm to 500 Ohm·cm at 500° C.

For example, the electrically conductive particles have a resistivity ranging from 0.005 to 400 Ohm·cm at 500° C., preferably ranging from 0.01 to 300 Ohm·cm at 500° C.; more preferably ranging from 0.05 to 150 Ohm·cm at 500° C. and most preferably ranging from 0.1 to 100 Ohm·cm at 500° C.

For example, the electrically conductive particles have a resistivity of at least 0.005 Ohm·cm at 500° C.; preferably of at least 0.01 Ohm·cm at 500° C., more preferably of at least 0.05 Ohm·cm at 500° C.; even more preferably of at least 0.1 Ohm·cm at 500° C., and most preferably of at least 0.5 Ohm·cm at 500° C.

For example, the electrically conductive particles have a resistivity of at most 400 Ohm·cm at 500° C.; preferably of at most 300 Ohm·cm at 500° C., more preferably of at most 200 Ohm·cm at 500° C.; even more preferably of at most 150 Ohm·cm at 500° C., and most preferably of at most 100 Ohm·cm at 500° C.

For example, the particles of the bed have an average particle size ranging from 5 to 300 μm as determined by sieving according to ASTM D4513-11, preferably ranging from 10 to 200 μm and more preferably ranging from 20 to 200 μm or from 30 to 150 μm.

For example, the electrically conductive particles of the bed have an average particle size ranging from 5 to 300 μm as determined by sieving according to ASTM D4513-11, preferably ranging from 10 to 200 μm and more preferably ranging from 20 to 200 μm or from 30 to 150 μm.

For example, the particles of a catalytic composition have an average particle size ranging from 5 to 300 μm as determined by sieving according to ASTM D4513-11, preferably ranging from 10 to 200 μm and more preferably ranging from 20 to 200 μm or from 30 to 150 μm.

The electrical resistance is measured by a four-probe DC method using an ohmmeter. A densified power sample is shaped in a cylindrical pellet that is placed between the probe electrodes. Resistivity is determined from the measured resistance value, R, by applying the known expression ρ=R×A/L, where L is the distance between the probe electrodes typically a few millimetres and A the electrode area.

The solid particulate material can exhibit electronic, ionic or mixed electronic-ionic conductivity. The ionic bonding of many refractory compounds allows for ionic diffusion and correspondingly, under the influence of an electric field and appropriate temperature conditions, ionic conduction.

The electrical conductivity, σ, the proportionality constant between the current density j and the electric field E, is given by $$\sigma = j/E = \Sigma c_i \times Z_i q \times \mu_i$$

where $c_i$ is the carrier density (number/cm$^3$), $\mu_i$ the mobility (cm$^2$/Vs), and $Z^i q$ the charge (q=1.6×0$^{-19}$ C) of the ith charge carrier. The many orders of magnitude differences in σ between metals, semiconductors and insulators generally result from differences in c rather than μ. On the other hand, the higher conductivities of electronic versus ionic conductors are generally due to the much higher mobilities of electronic versus ionic species.

The most common materials that can be used for resistive heating can be subdivided into nine groups:
(1) Metallic alloys for temperatures up to 1200-1400° C.,
(2) non-metallic resistors like silicon carbide (SiC), molybdenum disilicide (MoSi$_2$), nickel silicide (NiSi), sodium silicide (Na$_2$Si), magnesium silicide (Mg$_2$Si), platinum silicide (PtSi), titanium silicide (TiSi$_2$) and tungsten silicide (WSi$_2$) up to 1600-1900° C.,
(3) several mixed oxides and/or mixed sulphides being doped with one or more lower-valent cations with variable temperature optima,
(4) carbons like graphite up to 2000° C.,
(5) metallic carbides,
(6) transition metal nitrides,
(7) metallic phosphides,
(8) superionic conductors and
(9) phosphate electrolytes.

A first group of metallic alloys, for temperatures up to 1150-1250° C., is constituted by Ni—Cr alloys with low Fe content (0.5-2.0%), preferably alloy Ni—Cr (80% Ni, 20% Cr) and (70 Ni, 30% Cr). Increasing the content of Cr increases the material resistance to oxidation at high temperatures. A second group of metallic alloys having three components are Fe—Ni—Cr alloys, with maximum operating temperature in an oxidizing atmosphere to 1050-1150° C. but which can be conveniently used in reducing atmospheres or Fe—Cr—Al (chemical composition 15-30% Cr, 2-6% Al and Fe balance) protecting against corrosion by a surface layer of oxides of Cr and Al, in oxidizing atmospheres can be used up to 1300-1400° C. Silicon carbide as non-metallic resistor can exhibit wide ranges of resistivity that can be controlled by the way they are synthesized and the presence of impurities like aluminium, iron, oxide, nitrogen or extra carbon or silicon resulting in non-stoichiometric silicon carbide. In general silicon carbide has a high resistivity at low temperature but has good resistivity in the range of 500 to 1200° C. In an alternative embodiment, the non-metallic resistor can be devoid of silicon carbide, and/or can comprise molybdenum disilicide (MoSi$_2$), nickel silicide (NiSi), sodium silicide (Na$_2$Si), magnesium silicide (Mg$_2$Si), platinum silicide (PtSi), titanium silicide (TiSi$_2$), tungsten silicide (WSi$_2$) or a mixture thereof.

Graphite and amorphous carbon (like coke, petroleum coke, and/or carbon black) have rather low resistivity values, with a negative temperature coefficient up to about 600° C. after which the resistivity starts to increase.

Many mixed oxides and/or mixed sulphides being doped with one or more lower-valent cations, having in general too high resistivity at low temperature, become ionic or mixed conductors at high temperature. The following circumstances can make oxides sufficient conductors for heating purposes: ionic conduction in solids is described in terms of the creation and motion of atomic defects, notably vacancies and interstitials of which its creation and mobility is very positively dependent on temperature. Such mixed oxides are ionic conductors, namely being doped with one or more lower-valent cations. Three mechanisms for ionic defect formation in oxides are known: (1) Thermally induced intrinsic ionic disorder (such as Schottky and Frenkel defect pairs resulting in non-stoichiometry), (2). Redox-induced defects and (3) Impurity-induced defects. The first two categories of defects are predicted from statistical thermodynamics and the latter form to satisfy electroneutrality. In the latter case, high charge carrier densities can be induced by substituting lower valent cations for the host cations. Mixed oxides and/or mixed sulphides with fluorite, pyrochlore or perovskite structure are very suitable for substitution by one or more lower-valent cations.

Several sublattice disordered oxides or sulphides have high ion transport ability at increasing temperature. These are superionic conductors, such as LiAlSiO$_4$, Li$_{10}$GeP$_2$S$_{12}$, Li$_{3.6}$Si$_{0.6}$P$_{0.4}$O$_4$, NaSICON (sodium (Na) Super Ionic CONductor) with the general formula Na$_{1+x}$Zr$_2$P$_{3-x}$Si$_x$O$_{12}$ with 0<x<3, for example $Na_3Zr_2PSi_2O_{12}$ (x=2), or sodium beta alumina, such as $NaA_{11}O_{17}$, $Na_{1.6}Al_{11}O_{17.3}$, and/or $Na_{1.76}Li_{0.38}Al_{10.62}O_{17}$.

High concentrations of ionic carriers can be induced in intrinsically insulating solids and creating high defective solids. Thus, the electrically conductive particles of the bed are or comprise one or more mixed oxides being an ionic or mixed conductor, namely being doped with one or more lower-valent cations and/or one or more mixed sulphides being an ionic or mixed conductor, namely being doped with one or more lower-valent cations. With preference, the mixed oxides are selected from one or more oxides having a cubic fluorite structure being at least partially substituted with one or more lower-valent cations, preferentially selected from Sm, Gd, Y, Sc, Yb, Mg, Ca, La, Dy, Er, Eu; and/or from one or more $ABO_3$-perovskites with A and B tri-valent cations, being at least partially substituted in A position with one or more lower-valent cations, preferentially selected from Ca, Sr, or Mg, and comprising at least one of Ni, Ga, Co, Cr, Mn, Sc, Fe and/or a mixture thereof in B position; and/or from one or more $ABO_3$-perovskites with A bivalent cation and B tetra-valent cation, being at least partially substituted with one or more lower-valent cations, preferentially selected from Mg, Sc, Y, Nd or Yb in the B position or with a mixture of different B elements in the B position; and/or from one or more $A_2B_2O_7$-pyrochlores with A trivalent cation and B tetra-valent cation being at least partially substituted in A position with one or more lower-valent cations, preferentially selected from Ca or Mg, and comprising at least one of Sn, Zr and Ti in B position.

With preference, the one or more mixed sulphides are selected from one or more sulphides having a cubic fluorite structure being at least partially substituted with one or more lower-valent cations, preferentially selected from Sm, Gd, Y, Sc, Yb, Mg, Ca, La, Dy, Er, Eu; and/or from one or more $ABS_3$ structures with A and B tri-valent cations, being at least partially substituted in A position with one or more lower-valent cations, preferentially selected from Ca, Sr, or Mg, and comprising at least one of Ni, Ga, Co, Cr, Mn, Sc, Fe and/or a mixture thereof in B position; and/or from one or more $ABS_3$ structures with A bivalent cation and B tetra-valent cation, being at least partially substituted with one or more lower-valent cations, preferentially selected from Mg, Sc, Y, Nd or Yb in the B position or with a mixture of different B elements in the B position; and/or from one or more $A_2B_2S_7$ structures with A trivalent cation and B tetra-valent cation being at least partially substituted in A position with one or more lower-valent cations, preferentially selected from Ca or Mg, and comprising at least one of Sn, Zr and Ti in B position.

With preference, the one or more mixed sulphides are selected from one or more $ABS_3$ structures with A and B tri-valent cations, being at least partially substituted in A position with one or more lower-valent cations, preferentially selected from Ca, Sr, or Mg, and comprising at least Ni, Ga, Co, Cr, Mn, Sc, Fe and/or a mixture thereof in B position; and/or from one or more $ABS_3$ structures with A bivalent cation and B tetra-valent cation, being at least partially substituted with one or more lower-valent cations, preferentially selected from Mg, Sc, Y, Nd or Yb in the B position or with a mixture of different B elements in the B position; and/or from one or more $A_2B_2S_7$ structures with A trivalent cation and B tetra-valent cation being at least partially substituted in A position with one or more lower-valent cations, preferentially selected from Ca or Mg, and comprising at least Sn, Zr and Ti in B position.

With preference, the degree of substitution in the one or more mixed oxides doped with one or more lower-valent cations and having a cubic fluorite structure is between 1 and 15 atom % based on the total number of atoms present in the one or more oxides having a cubic fluorite structure, preferably between 3 and 12 atom %, more preferably between 5 and 10 atom %.

With preference, the degree of substitution in the one or more mixed oxides doped with one or more lower-valent cations is between 1 and 50 atom % based on the total number of atoms present in the one or more $ABO_3$-perovskites with A and B tri-valent cations, in the one or more $ABO_3$-perovskites with A bivalent cation and B tetra-valent cation or in the one or more $A_2B_2O_7$-pyrochlores with A trivalent cation and B tetra-valent cation respectively, preferably between 3 and 20 atom %, more preferably between 5 and 15 atom %.

With preference, the degree of substitution in the one or more mixed sulphides doped with one or more lower-valent cations and having a cubic fluorite structure is between 1 and 15 atom % based on the total number of atoms present in the one or more oxides having a cubic fluorite structure, preferably between 3 and 12 atom %, more preferably between 5 and 10 atom %.

With preference, the degree of substitution in the one or more mixed sulphides doped with one or more lower-valent cations is between 1 and 50 atom % based on the total number of atoms present in the one or more $ABS_3$ structures with A and B tri-valent cations, in the one or more $ABS_3$ structures with A bivalent cation and B tetra-valent cation or in the one or more $A_2B_2S_7$ structures with A trivalent cation and B tetra-valent cation respectively, preferably between 3 and 20 atom %, more preferably between 5 and 15 atom %.

Said one or more oxides having a cubic fluorite structure, said one or more $ABO_3$-perovskites with A and B tri-valent cations, said one or more $ABO_3$-perovskites with A bivalent cation and B tetra-valent cation or said one or more $A_2B_2O_7$-pyrochlores with A trivalent cation and B tetra-valent cation being at least partially substituted with lower valent cations, said one or more sulphides having a cubic fluorite structure, said one or more $ABS_3$ structures with A and B tri-valent cations, said one or more $ABS_3$ structures with A bivalent cation and B tetra-valent cation, said one or more $A_2B_2S_7$ structures with A trivalent cation and B tetra-valent cation being at least partially substituted with lower valent cations also means that the same element, being a high-valent cation, can be reduced in the lower-valent equivalent, for example, Ti(IV) can be reduced in Ti(III) and/or Co(III) can be reduced in Co(II) and/or Fe(III) can be reduced in Fe(II) and/or Cu(II) can be reduced in Cu(I).

Phosphate electrolytes such as $LiPO_4$ or $LaPO_4$ can also be used as electrically conductive particles.

Metallic carbides, transition metal nitrides and metallic phosphides can also be selected as electrically conductive particles. For example, metallic carbides are selected from iron carbide ($Fe_3C$), molybdenum carbide (mixture of MoC and $Mo_2C$). For example, said one or more transition metal nitrides are selected from zirconium nitride (ZrN), tungsten nitride (mixture of $W_2N$, WN, and $WN_2$), vanadium nitride (VN), tantalum nitride (TaN), and/or niobium nitride (NbN). For example, said one or more metallic phosphides are selected from copper phosphide ($Cu_3P$), indium phosphide (InP), gallium phosphide (GaP), sodium phosphide $Na_3P$), aluminium phosphide (AlP), zinc phosphide ($Zn_3P_2$) and/or calcium phosphide ($Ca_3P_2$).

For example, the electrically conductive particles of the bed are or comprise silicon carbide. For example, at least 10 wt. % of the electrically conductive particles based on the total weight of the particles of the bed are silicon carbide particles and have a resistivity ranging from 0.001 Ohm·cm to 500 Ohm·cm at of 500° C.

In the embodiment wherein the electrically conductive particles of the bed are or comprise silicon carbide, the person skilled in the art will have the advantage to conduct a step of pre-heating with a gaseous stream said fluidized bed reactor before conducting said endothermic reaction in the fluidized bed reactor. Advantageously, the gaseous stream is a stream of inert gas, i.e., nitrogen, argon, helium, methane, carbon dioxide or steam. The temperature of the gaseous stream can be at least 500° C., or at least 550° C., or at least 600° C., or at least 650° C., or at least 700° C. Advantageously, the temperature of the gaseous stream can be comprised between 500° C. and 700° C., for example between 525° C. and 675° C. Said gaseous stream of inert gas can also be used as the fluidification gas. The pre-heating of the said gaseous stream of inert gas is performed thanks to conventional means, including using electrical energy. The temperature of the gaseous stream used for the preheating of the bed doesn't need to reach the temperature reaction.

Indeed, the resistivity of silicon carbide at ambient temperature is high, to ease the starting of the reaction, it may be useful to heat the fluidized bed by external means, as with preference the fluidized bed reactor is devoid of heating means. Once the bed is heated at the desired temperature, the use of a hot gaseous stream may not be necessary.

However, in an embodiment, the electrically conductive particles of the bed are or comprise a mixture of silicon carbide particles and electrically conductive particles different from silicon carbide particles.

The pre-heating step may be also used in the case wherein electrically conductive particles different from silicon carbide particles are present in the bed. For example, it may be used when the content of silicon carbide in the electrically conductive particles of the bed is more than 80 wt. % based on the total weight of the electrically conductive particles of the bed, for example, more than 85 wt. %, for example, more than 90 wt. %, for example, more than 95 wt. %, for example, more than 98 wt. %, for example, more than 99 wt. %. However, a pre-heating step may be used whatever is the content of silicon carbide particles in the bed.

In the embodiment wherein the electrically conductive particles of the bed are or comprise a mixture of silicon carbide particles and electrically conductive particles different from silicon carbide particles, the electrically conductive particles of the bed may comprise from 10 wt. % to 99 wt. % of silicon carbide particles based on the total weight of the electrically conductive particles of the bed; preferably, from 15 wt. % to 95 wt. %, more preferably from 20 wt. % to 90 wt. %, even more preferably from 25 wt. % to 80 wt. % and most preferably from 30 wt. % to 75 wt. %.

For example, the electrically conductive particles of the bed are or comprise a mixture of silicon carbide particles and electrically conductive particles different from silicon carbide particles and the electrically conductive particles of the bed comprises at least 40 wt. % of silicon carbide particles based on the total weight of the electrically conductive particles of the bed; preferably at least 50 wt. %, more preferably at least 60 wt. %, even more preferably at least 70 wt. % and most preferably at least 80 wt. %.

In an embodiment, the electrically conductive particles of the bed may comprise from 10 wt. % to 90 wt. % of electrically conductive particles different from silicon carbide particles based on the total weight of the electrically conductive particles of the bed; preferably, from 15 wt. % to 95 wt. %, more preferably from 20 wt. % to 90 wt. %, even more preferably from 25 wt. % to 80 wt. % and most preferably from 30 wt. % to 75 wt. %.

However, it may be interesting to keep the content of electrically conductive particles different from silicon carbide particles quite low in the mixture. Thus, in an embodiment, the electrically conductive particles of the bed comprise a mixture of silicon carbide particles and electrically conductive particles different from silicon carbide particles and electrically conductive particles of the bed comprises from 1 wt. % to 20 wt. % of electrically conductive particles different from silicon carbide based on the total weight of the electrically conductive particles of the bed; preferably, from 2 wt. % to 15 wt. %, more preferably, from 3 wt. % to 10 wt. %, and even more preferably, from 4 wt. % to 8 wt. %.

For example, the electrically conductive particles of the bed are or comprise a mixture of silicon carbide particles and electrically conductive particles different from silicon carbide particles and the said electrically conductive particles different from silicon carbide particles are particles selected from graphite, carbon black, coke, petroleum coke and/or any mixture thereof. For example, the said electrically conductive particles different from silicon carbide particles are or comprise graphite.

Thus, in an embodiment, the electrically conductive particles are a combination of silicon carbide particles and graphite particles. Such electrically conductive particles, upon the electrification of the fluidized bed reactor, will heat up and because of their fluidification, will contribute to the raise and/or to the maintaining of the temperature within the reactor. The Joule heating of such electrically conductive material allows accelerating the heating of the reactant and/or of the catalyst that is present within the fluidized bed reactor.

When graphite is selected, it can preferably be flake graphite. It is also preferable that the graphite has an average particle size ranging from 1 to 400 µm as determined by sieving according to ASTM D4513-11, preferably from 5 to 300 µm, more preferably ranging from 10 to 200 µm and most preferably ranging from 20 to 200 µm or from 30 to 150 µm.

The presence of electrically conductive particles different from silicon carbide particles in the bed allows applying the process according to the disclosure with or without the pre-heating step, preferably without the pre-heating step. Indeed, the electrically conductive particles, upon the electrification of the fluidized bed reactor, will heat up and because of their fluidification, will contribute to raising and/or maintaining the desired temperature within the reactor.

The Silicon Carbide Particles

For example, the silicon carbide is selected from sintered silicon carbide, nitride-bounded silicon carbide, recrystallised silicon carbide, reaction bonded silicon carbide and any mixture thereof.

Sintered SiC (SSiC) is a self-bonded material containing a sintering aid (typically boron) of less than 1% by weight.

Recrystallized silicon carbide (RSiC), a high purity SiC material sintered by the process of evaporation-condensation without any additives.

Nitride-bonded silicon carbide (NBSC) is made by adding fine silicon powder with silicon carbide particles or eventually in the presence of a mineral additive and sintering in a nitrogen furnace. The silicon carbide is bonded by the silicon nitride phase ($Si_3N_4$) formed during nitriding.

Reaction bonded silicon carbide (RBSC), also known as siliconized silicon carbide or SiSiC, is a type of silicon carbide that is manufactured by a chemical reaction between porous carbon or graphite with molten silicon. The silicon reacts with the carbon forming silicon carbide and bonds the silicon carbide particles. Any excess silicon fills the remaining pores in the body and produces a dense SiC—Si composite. Due to the left-over traces of silicon, reaction bonded silicon carbide is often referred to as siliconized silicon carbide. The process is known variously as reaction bonding, reaction sintering, self-bonding, or melt infiltration.

In general, high purity SiC particles have a resistivity above 1000 Ohm·cm, whereas sintered, reaction bonded and nitride-bonded can exhibit resistivities of about 100 to 1000 depending on the impurities in the SiC phase. Electrical resistivity of bulk polycrystalline SiC ceramics shows a wide range of resistivity depending on the sintering additive and heat-treatment conditions (Journal of the European Ceramic Society, Volume 35, Issue 15, December 2015, Pages 4137; Ceramics International, Volume 46, Issue 4, March 2020, Pages 5454). SiC polytypes with high purity possess high electrical resistivity ($>10^6$ Ω·cm) because of their large bandgap energies. However, the electrical resistivity of SiC is affected by doping impurities. N and P act as n-type dopants and decrease the resistivity of SiC, whereas Al, B, Ga, and Sc act as p-type dopants. SiC doped with Be, O, and V are highly insulating. N is considered the most efficient dopant for improving the electrical conductivity of SiC. For N doping of SiC (to decrease resistivity) $Y_2O_3$ and $Y_2O_3$-$REM_2O_3$ (REM=rare earth metal=Sm, Gd, Lu) have been used as sintering additives for efficient growth of conductive SiC grains containing N donors. N-doping in SiC grains was promoted by the addition of nitrides (AlN, BN, $Si_3N_4$, TiN, and ZrN) or combinations of nitrides and $REM_2O_3$ (AlN—$REM_2O_3$ (REM=rare earth metal=Sc, Nd, Eu, Gd, Ho, and Er) or TiN—$Y_2O_3$).

The Catalytic Composition

The choice of the catalytic composition is dependent on the reaction performed.

For example, the process to perform a dehydrogenation and/or aromatisation of hydrocarbons having at least two carbons to produce olefins and/or aromatics is selected from paraffin dehydrogenation, alkyl-aromatic dehydrogenation, naphtha reforming, or paraffin aromatisation.

Examples of commercially available catalysts to perform propane dehydrogenation are DeH-26 (UOP) and CATOFIN™ (Clariant).

Paraffin Dehydrogenation:

In one or more embodiments, the paraffin dehydrogenation catalyst may include gallium, zinc, chromium, iron and/or group VIII metal or mixtures thereof, carried on a refractory oxide support, and may optionally comprise silicon, tin, germanium, lead, indium, gallium, thallium and mixtures of alkali or alkaline earth metal compounds.

In a preferred embodiment, the catalyst for the paraffin dehydrogenation reaction comprises essentially gallium (values are on dry final catalyst composition basis, balance to 100 wt. % being the carrier, like alumina with gamma, delta, theta or alpha phase):
  (i) from 0.1 to 25 wt. %, preferably 0.2 to 3.0 wt. %, of gallium oxide ($Ga_2O_3$);
  (ii) from 1 to 300 weight parts per million (wppm), preferably 50 to 300 wppm of platinum;
  (iii) from 0 to 4 wt. %, preferably 0.01 to 1 wt. %, of an alkali metal and/or alkaline earth metal such as potassium;
  (iv) from 0.1 to 4 wt. % silicon oxide;

In another preferred embodiment, the catalyst for the paraffin dehydrogenation reaction is based on chromium and comprises (values are on dry final catalyst composition basis, balance to 100 wt. % being the carrier, like alumina with gamma, delta, theta or alpha phase):
  (i) from 1 to 30 wt. %, preferably, from 10 to 25 wt. %, of chromium oxide ($Cr_2O_3$);
  (ii) optionally, from 0.1 to 3.5 wt. %, most preferably, from 0.2 to 2.5 wt. %, of tin oxide (SnO);
  (iii) from 0.2 to 3 wt. %, most preferably, from 0.5 to 2.0 wt. %, of an alkali or alkaline earth metal oxide, for example, potassium oxide;
  (iv) from 0.1 to 4 wt. % silicon oxide;

In another preferred embodiment, the catalyst for the paraffin dehydrogenation reaction may comprise essentially iron (values are on dry final catalyst composition basis, balance to 100 wt. % being the carrier, like alumina with gamma, delta, theta or alpha phase):
  (i) from 1 to 50 wt. %, preferably from 2 to 30 wt. %, of iron oxide;
  (ii) from 0.1 to 20 wt. %, preferably from 0.5 to 10 wt. %, of at least one alkali or alkaline earth metal oxide, more preferably, potassium oxide;
  (iii) from 0 to 10 wt. %, preferably, from 0.1 to 5 wt. %, of at least one rare earth oxide, preferably selected from the group comprising cerium oxide, lanthanum oxide, praseodymium oxide, and mixtures thereof;

In another preferred embodiment, the catalyst for the paraffin dehydrogenation reaction may comprise essentially group VIII metals (values are on dry final catalyst composition basis, balance to 100 wt. % being the carrier, like alumina with gamma, delta, theta or alpha phase):
  (i) 0.01 to 5.0 wt. % Group VIII noble metal, preferably 0.05 to 3.0 wt. %, especially about 0.1 to about 2.0 wt. % selected from the group comprising platinum, palladium, iridium, rhodium, osmium, ruthenium, or mixtures thereof. Platinum is the preferred Group VIII noble metal component;
  (ii) The alkali or alkaline earth component (as oxide or carbonate) preferably comprise between 0.7 and 1.5 wt. %, or between 0.8 to 1.2 wt. %. They may be selected from the group comprising caesium, rubidium, potassium, sodium, and lithium or from the group comprising barium, strontium, calcium, and magnesium or mixtures of metals. Potassium is the preferred second catalytic component;
  (iii) 0.01 to about 10 wt. %, preferably 0.1 to 5 wt. % of metal components selected from the group comprising tin, germanium, lead, indium, gallium, thallium, and mixtures thereof. This third metal component of the present disclosure preferably is tin;
  (iv) A halogen component comprising from 0.01 wt. % to about 15 wt. % of the group fluorine, chlorine, bromine, or iodine, or mixtures thereof. Chlorine is the preferred halogen components.

Other suitable particulate catalyst carriers are refractory oxides such as alumina (gamma, delta, theta or alpha phase), titania, zirconia, hafnia, lanthania, magnesia, ceria, preferably zirconia stabilized with magnesia, lanthania, yttria or ceria; metal-aluminates such as calcium aluminate and magnesium aluminate; and mixtures thereof. Particularly preferred particulate catalyst supports comprise alumina and/or stabilized zirconia, e.g. lanthania-stabilized alumina, ceria-zirconia-alumina, ceria-titania-alumina and ceria-magnesia-alumina materials. Preferred support materials are those common materials (mentioned above) that can be used for resistive heating at the same time and which can be subdivided into two main groups: (1) Metallic alloys and (2) non-metallic resistors like Silicon carbide (SiC) and Molybdenum disilicide (MoSi$_2$), several mixed oxides with variable temperature optima and carbons like graphite. This latter option results in intimate contact between the catalytic active metal and the resistor particulate material.

Alkyl-Aromatic Dehydrogenation:

The alkyl-aromatic dehydrogenation is selected from ethylbenzene dehydrogenation, ethylnaphthalene dehydrogenation, isopropylbenzene dehydrogenation or diethylbenzene dehydrogenation Ethylbenzene, ethylnaphthalene, isopropylbenzene or diethylbenzene dehydrogenation catalysts comprise the following components, based on the total weight of the catalyst:
- (i) from 50 to 85 wt. % Fe$_2$O$_3$, preferably from 60 to 80 wt. %
- (ii) from 3 to 25 wt. % K$_2$O, preferably from 4 to 20 wt. %
- (iii) Optionally from 0.1 to 5 wt. % MoO$_3$, preferably from 0.5 to 4 wt. %
- (iv) from 3 to 30 wt. % CeO$_2$, preferably from 5 to 25 wt. %
- (v) from 0.1 to 5 wt. % CaO, preferably from 0.5 to 4 wt. %
- (vi) from 0.1 to 5 wt. % Na$_2$O, preferably from 0.5 to 4 wt. %
- (vii) Optionally from 0.1 to 5 wt. % MnO$_2$, preferably from 0.5 to 4 wt. %
- (viii) from 0.1 to 150 ppm of at least one element of Pb, Pt, Os, Ir, Ru, Re, Pd, Ag, Au, Sn;
- (ix) Optionally from 0.1 to 40 wt. % solid carbon, like graphite, carbon black, petcoke or graphene
- (x) Furthermore, as an additional promoter, it contains from 0.001 to 5.0 wt. % of at least one oxide selected from the group comprising magnesium, titanium, zirconium, vanadium, niobium, chrome, tungsten, cobalt, nickel, copper, zinc, boron, aluminum, gallium, indium, silicon, germanium, tin, phosphorus, antimony, bismuth, yttrium, lanthanum, praseodymium, neodymium, dysprosium and samarium.

Alkyl-aromatic dehydrogenation catalysts are generally binderless and composed of the elements listed above. Examples of commercially available catalysts are FlexiCat Gold®-2 S3 (BASF) and StyroMax® (Clariant).

In a particular embodiment of the present disclosure binderless composition can also be mixed with electrically conducting materials to form particulate material, being those common materials (mentioned above) that can be used for resistive heating at the same time and which can be subdivided into two main groups: (1) Metallic alloys and (2) non-metallic resistors like Silicon carbide (SiC) and Molybdenum disilicide (MoSi$_2$), several mixed oxides with variable temperature optima and carbons like graphite. This latter option results in intimate contact between the catalytic active metal and the resistor particulate material.

Naphtha Reforming:

Naphtha reforming catalysts are bifunctional catalysts comprising of a hydrogenation-dehydrogenation function and an acid function. The acid function, which is important for isomerization reactions, is generally associated with the porous refractory oxide which serves as the support for the metal component, usually a Group VIII noble metal, to which is generally attributed the hydrogenation-dehydrogenation function. The reforming catalysts comprise the following components (values are on dry final catalyst composition basis, balance to 100 wt. % being alumina (gamma, delta, theta or alpha phase):
- (i) 0.01 to about 3 wt. % Group VIII noble metal (palladium, platinum, iridium, rhodium, osmium, ruthenium and mixtures thereof) of the final catalytic composition, more preferably 0.1 to about 2 wt. %, especially about 0.1 to 1 wt. % platinum;
- (ii) 0.1 to about 3.5 wt. %, preferably about 0.5 to about 1.5 wt. % of halogen (fluoride, chloride, iodide, bromide, or mixtures thereof), particularly preferred is chloride;
- (iii) 0.01 to about 5 wt. %, preferably 0.1 to about 3 wt. % of one or more promoter metals selected from metals of Groups IIIA, IVA, IB, VIB, and VIIB, can be present as metal or oxide compound, especially about 0.07 to 1.5 wt. % of rhenium and/or 0.07 to 1.0 wt. % of tin;
- (iv) Optionally 0.1-40 wt. % solid carbon, like graphite, carbon black, petroleum coke or graphene;
- (v) Optionally 1 to about 30 wt. % of crystalline molecular sieves (i.e. one or more zeolites, silicoaluminophosphates), preferably 10 or 12 membered ring molecular sieves.

For example, the one or more zeolites are selected from the group of AFI, AFO, AEL, FAU, LTL, MFI, MEL, FER, MTT, MWW, MOR, TON, EUO, MFS, CON, MRE, MAZ, BEA and MTW families.

With preference, a zeolite from the AFI family is SAPO-5.

With preference, a zeolite from the AFO family is SAPO-41.

With preference, a zeolite from the AEL family is SAPO-11.

With preference, zeolites from the FAU family are SAPO-37, zeolite X, zeolite Y.

With preference, a zeolite from the LTL family is L-zeolite.

With preference, zeolites from the MFI family are ZSM-5, silicalite-1, boralite C, TS-1

With preference, zeolites from the MEL family are ZSM-11, silicalite-2, boralite D, TS-2, SSZ-46.

With preference, zeolites from the FER family are ferrierite, FU-9, ZSM-35.

With preference, a zeolite from the MTT family is ZSM-23.

With preference, zeolites from the MWW family are MCM-22, MCM-56, UZM-8, PSH-3, ITQ-1, MCM-49.

With preference, a zeolite from the MOR family is UZM-14.

With preference, zeolites from the TON family are ZSM-22, Theta-1, NU-10.

With preference, zeolites from the EUO family are ZSM-50, EU-1.

With preference, a zeolite from the MFS family is ZSM-54.

With preference, a zeolite from the CON family is CIT-1.

With preference, a zeolite from the MRE family is ZSM-48.

With preference, a zeolite from the MAZ family is omega zeolite.

With preference, a zeolite from the BEA family is beta zeolite.

With preference, a zeolite from the MTW family is ZSM-12.

The components (i), (ii) and (iii) are essential parts of naphtha reforming catalysts, the above-mentioned catalyst components can be mixed with electrically conducting materials to form the particulate catalyst material, being those common materials (mentioned above) that can be used for resistive heating at the same time and which can be subdivided into two main groups: (1) Metallic alloys and (2) non-metallic resistors like silicon carbide (SiC) and molybdenum disilicide (MoSi$_2$), several mixed oxides with variable temperature optima and carbons like graphite. This latter option results in intimate contact between the catalytic active metal and the resistor particulate material.

Paraffin Aromatisation:

Paraffin aromatisation catalyst comprises a formulated zeolite support wherein the formulated zeolite support comprises one or more zeolite crystals that are joined together by a binder. The term "zeolite" generally refers to crystalline metal aluminosilicates. These zeolites exhibit a network of tetravalent and trivalent metal oxide tetrahedra in which tetravalent and trivalent atoms are crosslinked in a three-dimensional framework by sharing oxygen atoms.

The paraffin aromatisation catalysts comprise the following components (values are on dry final catalyst composition basis, balance to 100 wt. % is the binder):

(i) from 5.0 to 90.0 wt. % of one or more zeolites comprising at least one 10-membered ring channel and based on the total weight of the catalyst composition, preferably from 20.0 to 80.0 wt. %, more preferably from 25.0 to 75.0 wt. % and/or from 5.0 to 90.0 wt. % of one or more zeolites comprising pores with a diameter of at least 0.5 nm as determined by argon adsorption and based on the total weight of the catalyst composition. For example, large pore crystalline zeolites include without limitation one or more zeolites selected from the group of FAU, MAZ, BEA, LTL, MFI, MOZ, MTW, NES, AFI, STO, CON, STF, IFR, SFF, and MOR families.

With preference, zeolites from the FAU family are zeolite X, zeolite Y, ZSM-20, USY, faujasite, REY, RE-USY, LZ-210-A, LZ-210-M, LZ-210-T.

With preference, zeolites from the MAZ family are omega zeolite, ZSM-4.

With preference, a zeolite from the BEA family is beta zeolite.

With preference, a zeolite from the LTL family is L-zeolite.

With preference, a zeolite from the MFI family is ZSM-5.

With preference, a zeolite from the MOZ family is ZSM-10.

With preference, a zeolite from the MTW family is ZSM-12.

With preference, a zeolite from the NES family is SSZ-37.

With preference, zeolites from the AFI family are ZSM-12, SSZ-24.

With preference, a zeolite from the STO family is SSZ-31.

With preference, a zeolite from the CON family is SSZ-33.

With preference, a zeolite from the STF family is SSZ-35.

With preference, zeolites from the IFR family are SSZ-42, MCM-58.

With preference, a zeolite from the SFF family is SSZ-44.

With preference, a zeolite from the MOR family is mordenite.

Another zeolite can be SSZ-41.

In an aspect, the large pore zeolite has an isotypic framework structure.

In a preferred embodiment, the formulated zeolite support comprises L-zeolite:

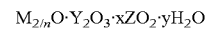

$M_{2/n}O \cdot Y_2O_3 \cdot xZO_2 \cdot yH_2O$ wherein "Y" designates aluminium, gallium or boron or mixtures thereof, "Z" designates silicon or germanium or mixtures thereof, "M" designates at least one exchangeable cation such as barium, calcium, cerium, lithium, magnesium, potassium, sodium, strontium and zinc or mixtures thereof. The "n" in the formula represents the valence of "M", "x" is 2 or greater; and "y" is the number of water molecules contained in the channels or interconnected voids with the zeolite.

(ii) The dehydrogenation activity is provided by one or more Group VIII metals added to the formulated zeolite in the range of 0.005 to 1 wt. %, preferably in the range of 0.05 to 0.5 wt. %. The metal is a Group VIII metal, Pt, Pd, Rh, Ir, Ru, Os, or combinations thereof; preferably platinum.

(iii) Or the dehydrogenation activity is provided by one or more of Ga, In, Zn, Cu, Re, Mo, and W or mixtures thereof, in the range of 0.05 to 10 wt. %, preferably 0.1 to 5 wt. %.

The metal may be added to the formulated zeolite by employing any suitable methodology, like ion-exchange, incipient wetness impregnation, or pore fill impregnation.

(iv) a halide in the range of 0.1 to 5 wt. %, preferably 0.2 to 3 wt. % including without limitation chloride, fluoride, bromide, iodide, or combinations thereof.

(v) Optionally, a rare earth element, including without limitation lanthanides, like cerium (Ce), praseodymium (Pr), neodymium (Nd), Promethium (Pm), Samarium (Sm), Europium (Eu), Gadolinium (Gd), Terbium (Tb), Dysprosium (Dy), Holmium (Ho), Erbium (Er), Thulium (Tm), Ytterbium (Yb), Lutetium (Lu), and the like (Scandium and yttrium), or combinations thereof. The rare earth element is present at about 0.1 to about 15 wt. %, preferably from about 0.2 to about 10 wt. %.

Other suitable particulate catalyst binders are refractory oxides such as clays, silica, alumina (gamma, delta, theta or alpha phase), titania, zirconia, hafnia, lanthania, magnesia, ceria, preferably zirconia stabilized with magnesia, lanthania, yttria or ceria; metal-aluminates such as calcium aluminate and magnesium aluminate; and mixtures thereof. Particularly preferred particulate catalyst binders comprise alumina and/or stabilized zirconia, e.g. lanthania-stabilized alumina, ceria-zirconia-alumina, ceria-titania-alumina and ceria-magnesia-alumina materials. Preferred binder materials are those common materials (mentioned above) that can be used for resistive heating at the same time and which can be subdivided into two main groups: (1) Metallic alloys and (2) non-metallic resistors like Silicon carbide (SiC) and Molybdenum disilicide (MoSi2), several mixed oxides with variable temperature optima and carbons like graphite. This latter option results in intimate contact between the catalytic active metal and the resistor particulate material.

The particulate catalyst support particles preferably have a particle size ranging from 5 to 300 μm, more preferably ranging from 10 to 200 μm and most preferably from 30 to 150 μm. The catalytic metal or metal precursors may be dispersed over the surface of the particulate catalyst support by conventional impregnation of soluble metal compounds onto the particulate catalyst support followed by drying and calcination to convert the catalytic metal compound or compounds to their respective oxides. Alternatively, the catalytic metal or metal precursors may be dispersed over the surface of the particulate catalyst support material by adsorption, precipitation, using metals sols, by mixing or by deposition-precipitation methods employing metal salts that deposit insoluble metal compounds on the particulate catalyst support from solution upon heating or combination thereof. Further, metal salts can be ion-exchanged with counter cations on the support material. The metal precursors are reduced, if required, into the metallic state at elevated temperature by using hydrogen, carbon monoxide or hydrocarbons as reductants. This can be done before loading the catalyst in the fluidised bed reactor or in situ in the fluidised bed before feeding the feedstock or during feeding the feedstock.

Dehydrogenation or Aromatisation Process:

The hydrocarbon stream, to be fed to the fluidized bed reactor, is vaporized in a vaporizer, which advantageously may be heated using heat contained in the reactor effluent. Before dehydrogenation and/or aromatisation, the feed gas stream is desulfurized, to prevent poisoning of the metal catalyst. For this purpose, the feed gas stream is passed through a desulfurization reactor containing NiO, CuO or ZnO as absorbent, in which $H_2S$ is converted to NiS, CuS or ZnS and $H_2O$ at temperatures of 200 to 400° C. In the case of liquid hydrocarbon feedstock, like naphtha-like feedstock (including hexane, heptane etc) catalytic desulfurization can be applied to decompose the organic sulphur compounds into inorganic sulphur with the help of hydrogen. The feed gas stream substantially free of sulfur, subsequently is mixed with steam and/or hydrogen, and preheated to a temperature of 300 to 700° C., preferably 450 to 600° C. The steam may be added to the vaporized hydrocarbon stream by direct injection or by use of a saturator. Subsequently, the feedstock mixture is heated to a temperature of 480 to 700° C. at pressures below 10 atmospheres by passing through the electrothermal fluidised bed dehydrogenation and/or aromatisation vessel containing the dehydrogenation and/or aromatisation catalyst. The gas stream leaving the fluidised bed reactor contains olefins, single-ring aromatics, $H_2$, unconverted steam and hydrocarbons as well as possibly inert gas constituents of the feed gas stream.

Dehydrogenation or aromatisation conditions include a temperature of from about 480° to about 700° C., a pressure of from about 0.01 to 10 atmospheres absolute, and a liquid hourly space velocity (LHSV) of from about 0.1 to 100 $hr^{-1}$. Generally, for normal paraffins, the lower the molecular weight, the higher the temperature required for comparable conversion. The pressure in the dehydrogenation zone is maintained as low as practicable, consistent with equipment limitations, to maximize the chemical equilibrium advantages. The dehydrogenatable or aromatisizable hydrocarbons may be admixed with a diluent material before, while, or after being passed to the dehydrogenation zone. The diluent material may be hydrogen, steam, methane, ethane, carbon dioxide, nitrogen, argon, and the like or a mixture thereof. Hydrogen and steam are the preferred diluents. When utilizing a diluent, it is utilized in a diluent-to-hydrocarbon mole ratio of about 0.1/1 to about 40/1, preferably about 0.4/1 to about 10/1. The diluent stream passed to the dehydrogenation zone will typically be recycled diluent separated from the effluent from the dehydrogenation zone in a separation zone.

For example, solid materials that exhibit only sufficiently low resistivity at high temperature that they can be heating by external means before reaching the high enough temperature where resistive heating with electricity overtakes or by mixing with a sufficiently low resistivity solid at a low temperature so that the combined resulting resistivity allows to heat the fluidized bed to the desired reaction temperature.

It is a preferred embodiment of the present disclosure to withdraw continuously or intermittently solid particulate material and particulate catalyst, containing carbonaceous depositions, from the electrothermal fluidised bed vessel, transporting it to a fluidised bed regeneration vessel, burning the carbonaceous depositions with a stream containing oxygen and optionally carbon dioxide and/or steam, transporting the at least partially regenerated solid particulate material and particulate catalyst back into the electrothermal fluidised bed reformer vessel.

It is a preferred embodiment of the present disclosure to recover the sensible and latent heat in the reactor effluent product to preheat the dehydrogenation and/or aromatisation feedstock (both the hydrocarbons, hydrogen and/or steam).

The Installation

The terms "bottom" and "top" are to be understood in relation to the general orientation of the installation or the fluidized bed reactor. Thus, "bottom" will mean greater ground proximity than "top" along the vertical axis. In the different figures, the same references designate identical or similar elements.

FIG. 1 illustrates a prior art fluidized bed reactor 1 comprising a reactor vessel 3, a bottom fluid nozzle 5 for the introduction of a fluidizing gas and a reaction fluid, an optional inlet 7 for the material loading, an optional outlet 9 for the material discharge and a gas outlet 11 and a bed 15. In the fluidized bed reactor 1 of FIG. 1 the heat is provided by pre-heating the reaction fluid by combustion of fossil fuels using heating means 17 arranged for example at the level of the line that provides the reactor with the fluidizing gas and the reaction fluid.

The installation of the present disclosure is now described with reference to FIGS. 2 to 5. For sake of simplicity, internal devices known by the person in the art that are used in fluidized bed reactors, like bubble breakers, deflectors, particle termination devices, cyclones, ceramic wall coatings, thermocouples, etc. . . . are not shown in the figures.

Figure 2:
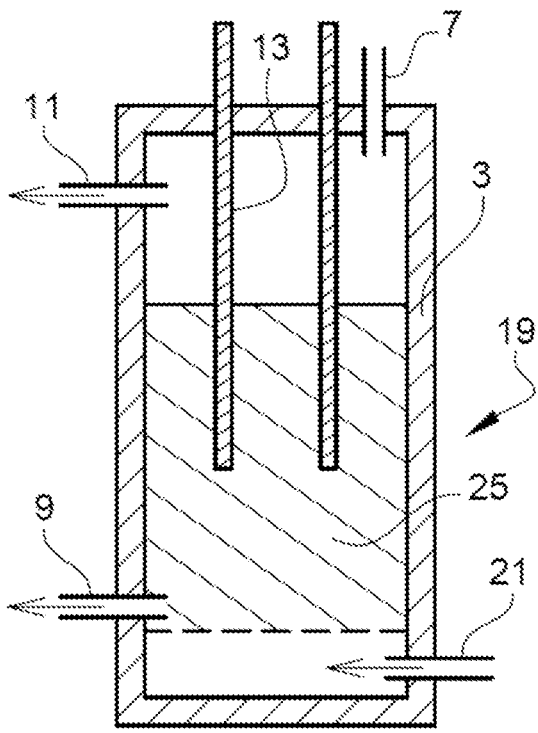
FIG. 2 illustrates an installation according to the disclosure with one reactor wherein the heating zone and reaction zone are the same.

FIG. 2 illustrates a first installation with a fluidized bed reactor 19 where the heating and reaction zone are the same. The fluidized bed reactor 19 comprises a reactor vessel 3, a bottom fluid nozzle 21 for the introduction of a fluidizing gas and a reaction fluid, an optional inlet 7 for the material loading, an optional outlet 9 for the material discharge and a gas outlet 11. The fluidized bed reactor 1 of FIG. 19 shows two electrodes 13 submerged in bed 25.

Figure 3:
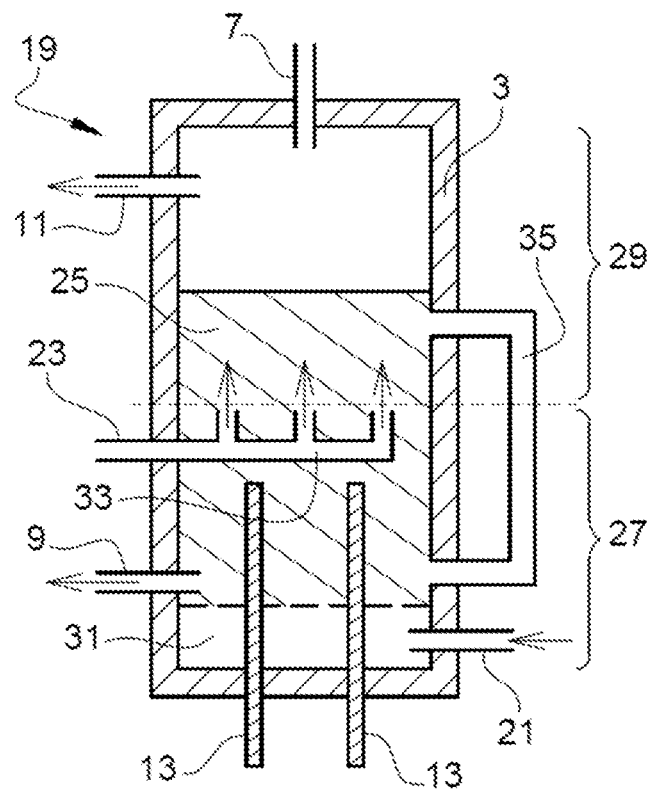
FIG. 3 illustrates an installation according to the disclosure with one reactor wherein the heating zone and reaction zone are arranged one above the other.

FIG. 3 illustrates an embodiment wherein at least one fluidized bed reactor 19 comprises a heating zone 27 and a reaction zone 29 with the heating zone 27 is the bottom zone and the reaction zone 29 is on top of the heating zone 27. One or more fluid nozzles 23 to provide a reaction fluid to the reaction zone from a distributor 33. As it can be seen in FIG. 3, the one or more fluid nozzles 23 can be connected to a distributor 33 to distribute the reaction fluid inside the bed 25.

Figure 4:
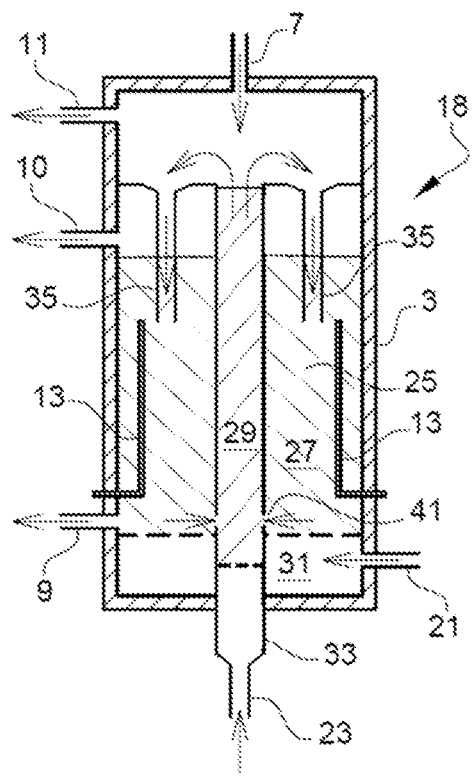
FIG. 4 illustrates an installation according to the disclosure with one reactor wherein the heating zone and reaction zone are arranged one lateral to the other.

FIG. 4 illustrates an installation wherein at least one fluidized bed reactor 18 comprises at least two lateral zones with the outer zone being the heating zone 27 and the inner zone being the reaction zone 29. The heated particles of the bed 25 from the outer zone are transferred to the inner zone by one or more openings 41 and mixed with the reaction fluid and optionally steam. At the end of the reaction zone, the particles are separated from the reaction product and transferred to the heating zone.

Figure 5:
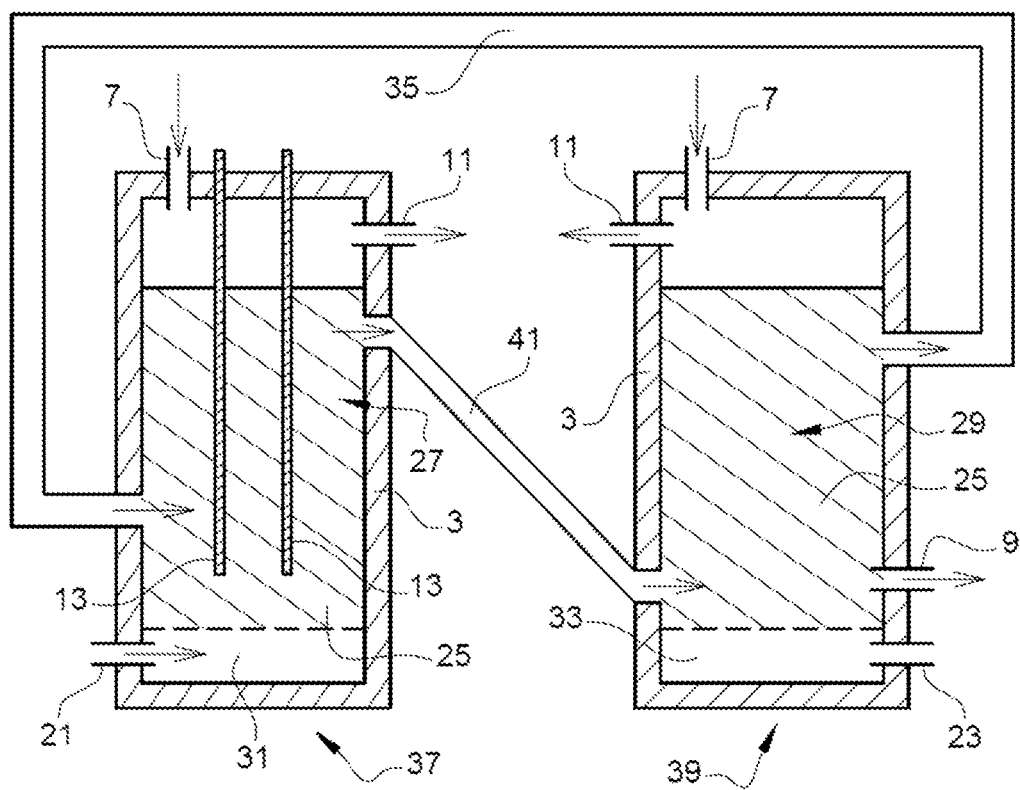
FIG. 5 illustrates an installation according to the disclosure with two reactors.

FIG. 5 illustrates the installation that comprises at least two fluidized bed reactors (37, 39) connected one to each other wherein at least one fluidized bed reactor is the heating zone 27 and one at least one fluidized bed reactor is the reaction zone 29.

The present disclosure also provides for an installation for a process to perform an endothermic dehydrogenation and/or aromatisation reaction, according to the first aspect, said installation comprising a vaporizer and at least one fluidized bed reactor (18, 19, 37, 39) arranged downstream the vaporizer, wherein the at least one fluidized bed reactor (18, 19, 37, 39) comprises:
at least two electrodes 13;
a reactor vessel 3;
one or more fluid nozzles (21, 23) for the introduction of a fluidizing gas and/or of a reaction fluid within at least one fluidized bed reactor (18, 19, 37, 39); and
a bed 25 comprising particles;
the installation is remarkable in that the particles of bed 25 comprise electrically conductive particles and particles of a catalytic composition, wherein at least 10 wt. % of the particles based on the total weight of the particles of bed 25 are electrically conductive particles and have a resistivity ranging from 0.001 Ohm·cm to 500 Ohm·cm at 500° C.; wherein the catalytic composition comprises one or more metallic compounds; with preference, the installation further comprises a desulfurization reactor arranged between the vaporizer and the fluidized bed reactor (18, 19, 37, 39).

For example, the electrically conductive particles of the bed are or comprise one or more particles selected from one or more metallic alloys, one or more non-metallic resistors, one or more metallic carbides, one or more transition metal nitrides, one or more metallic phosphides, one or more carbon-containing particles, one or more superionic conductors, one or more phosphate electrolytes, one or more mixed oxides being doped with one or more lower-valent cations, one or more mixed sulphides being doped with one or more lower-valent cations, and any mixture thereof.

In an embodiment, from 50 wt. % to 100 wt. % of the electrically conductive particles of the bed based on the total weight of the electrically conductive particles of the bed are one or more particles selected from one or more metallic alloys, one or more non-metallic resistors, one or more metallic carbides, one or more transition metal nitrides, one or more metallic phosphides, one or more carbon-containing particles, one or more superionic conductors, one or more phosphate electrolytes, one or more mixed oxides being doped with one or more lower-valent cations, one or more mixed sulphides being doped with one or more lower-valent cations, and any mixture thereof; preferably, from 60 wt. % to 100 wt. %; more preferably from 70 wt. % to 100 wt. %; even more preferably from 80 wt. % to 100 wt. % and most preferably from 90 wt. % to 100 wt. %.

With preference, the catalytic composition comprises:
one or more catalyst materials selected from gallium, zinc, chromium, iron, metal of the group VIII or mixtures thereof, and one or more catalytic supports; or
from 50 to 85 wt. % of $Fe_2O_3$ based on the total weight of the catalyst composition;
from 3 to 25 wt. % of $K_2O$; from 3 to 30 wt. % of $CeO_2$; from 0.1 to 5 wt. % of CaO; from 0.1 to 5 wt. % of $Na_2O$ and from 0.1 to 150 ppm of at least one element selected from Pb, Pt, Os, Ir, Ru, Re, Pd, Ag, Au, Sn or any mixture thereof; or
from 0.01 to 3.0 wt. % of one or more metals of the group VIII based on the total weight of the catalyst composition, from 0.1 to 3.5 wt. % of a halide; and from 0.01 to 5.0 wt. % of one or more metals selected from groups IIIA, IVA, IB, VIB and/or VIIB; or
from 5.0 to 90.0 wt. % of one or more zeolites comprising at least one 10-membered ring channel and based on the total weight of the catalyst composition, from 0.1 to 5.0 wt. % of a halide; and from 0.05 to 10.0 wt. % of one or more catalyst materials selected from Ga, In, Zn, Cu, Re, Mo, W; or from 0.005 to 1.0 wt. % of one or more metals of the group VIII or mixtures thereof based on the total weight of the catalyst composition.

For example, one electrode is a submerged central electrode or two electrodes 13 are submerged within the reactor vessel 3 of at least one reactor (18, 19, 37).

For example, the fluidizing gas is one or more diluent gases.

In a preferred embodiment, the at least one fluidized bed reactor (18, 19, 37, 39) is devoid of heating means. For example, at least one fluidized bed reactor is devoid of heating means selected from ovens, gas burners, hot plates, or any combination thereof. For example, all the fluidized bed reactors are devoid of heating means selected from ovens, gas burners, hot plates, or any combination thereof.

In a preferred embodiment, the at least one fluidized bed reactor comprising at least two electrodes and a bed comprising particles is devoid of packing.

For example, reactor vessel 3 has an inner diameter of at least 100 cm, or at least 200 cm; or at least 400 cm. Such large diameter allows to carry out the chemical reaction at an industrial scale, for example at a weight hourly space velocity of said reaction stream comprised between $0.1\ h^{-1}$ and $100\ h^{-1}$, preferably comprised between $1.0\ h^{-1}$ and $50\ h^{-1}$, more preferably comprised between $1.5\ h^{-1}$ and $10\ h^{-1}$, even more preferably comprised between $2.0\ h^{-1}$ and $6.0\ h^{-1}$. The weight hourly space velocity is defined as the ratio of mass flow of reaction stream to the mass of solid particulate material in the fluidized bed.

The at least fluidized bed reactor (18, 19, 37) comprises at least two electrodes 13. For example, one electrode is in electrical connection with the outer wall of the at least one fluidized bed reactor, while one additional electrode is submerged into the fluidized bed 25, or both electrodes 13 are submerged into the fluidized bed 25. Said at least two electrodes 13 are electrically connected and can be connected to a power supply (not shown). It is advantageous that said at least two electrodes 13 are made of carbon-containing material. The person skilled in the art will have an advantage that the electrodes 13 are more conductive than the particle bed 25.

For example, at least one electrode 13 is made of or comprises graphite; preferably, all or the two electrodes 13 are made of graphite. For example, one of the electrodes is the reactor vessel, so that the reactor comprises two electrodes, one being the submerged central electrode and one being the reactor vessel 3.

For example, the at least one fluidized bed reactor comprises at least one cooling device arranged to cool at least one electrode.

During use of the at least one fluidized bed reactor, an electric potential of at most 300 V is applied; preferably of at most 250 V; more preferably of at most 200 V, even more preferably of at most 150 V, most preferably at most 100 V, even most preferably of at most 90 V, or at most 80 V.

Thanks to the fact that the power of the electric current can be tuned, it is easy to adjust the temperature within the reactor bed.

One of the electrodes can be the reactor tube.

The reactor vessel 3 can be made of graphite. In an embodiment, it can be made of electro-resistive material that is silicon carbide or a mixture of silicon carbide and one or more carbon-containing materials.

With preference, reactor vessel 3 comprises reactor wall made of materials that are corrosion-resistant materials and advantageously said reactor wall materials comprise nickel (Ni), SiAlON ceramics, yttria-stabilized zirconia (YSZ), tetragonal polycrystalline zirconia (TZP) and/or tetragonal zirconia polycrystal (TPZ). SiAlON ceramics are ceramics based on the elements silicon (Si), aluminium (Al), oxygen (O) and nitrogen (N). They are solid solutions of silicon nitride ($Si_3N_4$), where Si—N bonds are partly replaced with Al—N and Al—O bonds.

For example, reactor vessel 3 is made of an electro-resistive material that is a mixture of silicon carbide and one or more carbon-containing materials; and the electro-resistive material of reactor vessel 3 comprises from 10 wt. % to 99 wt. % of silicon carbide based on the total weight of the electro-resistive material; preferably, from 15 wt. % to 95 wt. %, more preferably from 20 wt. % to 90 wt. %, even more preferably from 25 wt. % to 80 wt. % and most preferably from 30 wt. % to 75 wt. %.

For example, reactor vessel 3 is made of an electro-resistive material that is a mixture of silicon carbide and one or more carbon-containing materials; and the one or more carbon-containing materials are selected from graphite, carbon black, coke, petroleum coke and/or any mixture thereof; with preference, the carbon-containing material is or comprises graphite.

For example, reactor vessel 3 is not conductive. For example, reactor vessel 3 is made of ceramic.

For example, the at least one fluidized bed reactor (18, 19, 37, 39) comprises a heating zone 27 and a reaction zone 29, one or more fluid nozzles 23 to provide a reaction fluid to the reaction zone, and means 41 to transport the particles from the heating zone 27 to the reaction zone 29 when necessary, and optional means 35 to transport the particles from the reaction zone 29 back to the heating zone 27.

For example, as illustrated in FIG. 3, the at least one fluidized bed reactor is a single one fluidized bed reactor 19 wherein the heating zone 27 is the bottom part of the fluidized bed reactor 19 while the reaction zone 29 is the top part of the fluidised bed reactor 19; with preference, the installation comprises one or more fluid nozzles 23 to inject a reaction fluid between the two zones (27, 29) or in the reaction zone 29. The fluidized bed reactor 19 further comprises optionally an inlet 7 for the material loading, optionally an outlet 9 for the material discharge and a gas outlet 11. With preference, the fluidized bed reactor 19 is devoid of heating means. For example, electrodes 13 are arranged at the bottom part of the fluidized bed reactor 19, i.e. in the heating zone 27. For example, the top part of the fluidised bed reactor 19, i.e. the reaction zone 29, is devoid of electrodes. Optionally, the fluidized bed reactor 19 comprises means 35 to transport the particles from the reaction zone 29 back to the heating zone 27; such as by means of a line arranged between the top part and the bottom part of the fluidized bed reactor 19.

For example, as illustrated in FIG. 4, the installation comprises at least two lateral fluidized bed zones (27, 29) connected one to each other wherein at least one fluidized bed zone 27 is the heating zone and at least one fluidized bed zone 29 is the reaction zone. For example, the heating zone 27 is surrounding the reaction zone 29. With preference, the installation comprises one or more fluid nozzles 23 arranged to inject a reaction fluid and optionally steam to the at least one reaction zone 29 by means of a distributor 33. The fluidized bed zones (27, 29) further comprise optionally an inlet 7 for the material loading and a gas outlet 11. With preference, the at least one fluidized bed zone being the heating zone 27 and/or the at least one fluidized bed zone being the reaction zone 29 is devoid of heating means. For example, the at least one fluidized bed zone being the reaction zone 29 shows optionally an outlet 9 for the material discharge. One or more fluid nozzles 21 provide a fluidizing gas to at least the heating zone from a distributor 31. With one or more inlet devices 41, heated particles are transported from the heating zone 27 to the reaction zone 29, and with one or more means 35 comprising downcomers, the separated particles are transported from the reaction zone 29 back to the heating zone 27. The fluidization gas for the heating zone 27 can be an inert diluent, like one or more selected from steam, hydrogen, carbon dioxide, methane, ethane, argon, helium and nitrogen. In such a configuration, the fluidization gas for the heating zone can also comprise air or oxygen to burn deposited coke from the particles.

For example, as illustrated in FIG. 5, the installation comprises at least two fluidized bed reactors (37, 39) connected one to each other wherein at least one fluidized bed reactor 37 is the heating zone 27 and at least one fluidized bed reactor 39 is the reaction zone 29. With preference, the installation comprises one or more fluid nozzles 23 arranged to inject a reaction fluid and optionally steam to the at least one fluidized bed reactor 39 being the reaction zone 29. The fluidized bed reactors (37, 39) further comprise optionally an inlet 7 for the material loading and a gas outlet 11. With preference, the at least one fluidized bed reactor 37 being the heating zone 27 and/or the at least one fluidized bed reactor 39 being the reaction zone 29 is devoid of heating means. For example, the at least one fluidized bed reactor 39 being the reaction zone 29 shows optionally an outlet 9 for the material discharge. By means of the inlet device 41 heated particles are transported from the heating zone 27 to the reaction zone 29 when necessary, and by means of device 35 the separated particles after the reaction zone are transported from the reaction zone back to the heating zone. The fluidization gas for the heating zone can be an inert diluent, like one or more selected from steam, hydrogen, carbon dioxide, methane, ethane, argon, helium, and nitrogen. In such a configuration, the fluidization gas for the heating zone can also comprise air or oxygen to burn deposited coke from the particles.

For example, the at least one fluidized bed reactor 37 being the heating zone 27 comprises at least two electrodes 13 whereas the at least one fluidized bed reactor 39 being the reaction zone 29 is devoid of electrodes.

For example, the at least two fluidized bed reactors (37, 39) are connected one to each other by means 41 suitable to transport the particles from the heating zone 27 to the reaction zone 29, such as one or more lines.

For example, the at least two fluidized bed reactors (37, 39) are connected one to each other by means 35 suitable to transport the particles from the reaction zone 29 back to the heating zone 27, such as one or more lines.

The invention claimed is:

1. A process to perform an endothermic dehydrogenation and/or aromatization of hydrocarbons having at least two carbons to produce olefins and/or aromatics said process comprising the steps of:
   a) providing at least one fluidized bed reactor comprising at least two electrodes and a bed comprising particles;
   b) putting the particles of the bed in a fluidized state by passing upwardly through the said bed a vaporized fluid stream to obtain a fluidized bed;
   c) heating the fluidized bed to a temperature ranging from 480° C. to 700° C. to conduct the endothermic dehydrogenation and/or aromatisation reaction; and
   d) obtaining a reactor effluent containing hydrogen, unconverted hydrocarbons, and olefins and/or aromatics;
   characterized in that the particles of the bed comprise electrically conductive particles and particles of a catalytic composition, wherein at least 10 wt. % of the particles based on the total weight of the particles of the bed are electrically conductive particles and have a resistivity ranging from 0.001 Ohm·cm to 500 Ohm·cm at 500° C., wherein the catalytic composition comprises one or more metallic compounds;
   in that the void fraction of the bed is ranging from 0.5 to 0.8; in that the particles of the bed have an average particle size ranging from 5 to 300 μm as determined by sieving according to ASTM D4513-11; and in that the step (c) of heating the fluidized bed is performed by passing an electric current through the fluidized bed; further wherein:
   the process is a paraffin dehydrogenation process and the catalyst composition comprises one or more catalyst materials selected from gallium, zinc, chromium, iron, metal of the group VIII or mixtures thereof; and one or more catalytic supports; or
   that said process is an alkyl-aromatic dehydrogenation process and the catalyst composition comprises from 50 to 85 wt. % of $Fe_2O_3$ based on the total weight of the catalyst composition; from 3 to 25 wt. % of $K_2O$; from 3 to 30 wt. % of $CeO_2$; from 0.1 to 5 wt. % of CaO; from 0.1 to 5 wt. % of $Na_2O$ and from 0.1 to 150 ppm of at least one element selected from Pb, Pt, Os, Ir, Ru, Re, Pd, Ag, Au, Sn or any mixture thereof; or
   said process is a naphtha reforming process and the catalyst composition comprises from 0.01 to 3.0 wt. % of one or more metals of the group VIII based on the total weight of the catalyst composition; from 0.1 to 3.5 wt. % of a halide; and from 0.01 to 5.0 wt. % of one or more metals selected from groups IIIA, IVA, IB, VIB and/or VIIB; or
   said process is a paraffin aromatisation process and the catalyst composition comprises from 5.0 to 90.0 wt. % of one or more zeolites comprising at least one 10-membered ring channel and based on the total weight of the catalyst composition; from 0.1 to 5.0 wt. % of a halide; and from 0.05 to 10.0 wt. % of one or more catalyst materials selected from Ga, In, Zn, Cu, Re, Mo, W; or from 0.005 to 1.0 wt. % of one or more metals of the group VIII or mixtures thereof based on the total weight of the catalyst composition.

2. The process according to claim 1, characterized in that the electrically conductive particles of the bed are or comprise one or more particles selected from the group consisting of one or more metallic alloys, one or more non-metallic resistors, one or more metallic carbides, one or more transition metal nitrides, one or more metallic phosphides, one or more carbon-containing particles, one or more superionic conductors, one or more phosphate electrolytes, one or more mixed oxides being doped with one or more lower-valent cations, one or more mixed sulphides being doped with one or more lower-valent cations and/or any mixture thereof.

3. The process according to claim 1, characterized in that from 50 wt. % to 100 wt. % of the electrically conductive particles of the bed based on the total weight of the electrically conductive particles of the bed are one or more particles selected from the group consisting of one or more metallic alloys, one or more non-metallic resistors, one or more metallic carbides, one or more transition metal nitrides, one or more metallic phosphides, one or more carbon-containing particles, one or more superionic conductors, one or more phosphate electrolytes, one or more mixed oxides being doped with one or more lower-valent cations, one or more mixed sulphides being doped with one or more lower-valent cations, and any mixture thereof.

4. The process according to claim 1, characterized in that the electrically conductive particles of the bed are or comprise one or more non-metallic resistors selected from the group consisting of silicon carbide, molybdenum disilicide and a mixture thereof.

5. The process according to claim 1, characterized in that the electrically conductive particles of the bed are or comprise one or more mixed oxides being doped with one or more lower-valent cations that are one or more oxides having a cubic fluorite structure being at least partially substituted with one or more lower-valent cations.

6. The process according to claim 5, characterized in that said one or more lower-valent cations are selected from the group consisting of Sm, Gd, Y, Sc, Yb, Mg, Ca, La, Dy, Er, and Eu.

7. The process according to claim 5, characterized in that the mixed oxides being doped with one or more lower-valent cations are selected from the group consisting of:
   one or more $ABO_3$-perovskites with A and B tri-valent cations being at least partially substituted in A position with one or more lower-valent cations and comprising at least one of Ni, Ga, Co, Cr, Mn, Sc, Fe and/or a mixture thereof in B position, characterized in that said one or more lower-valent cations are selected from Ca, Sr, or Mg;
   one or more $ABO_3$-perovskites with A bi-valent cation and B tetra-valent cation, being at least partially substituted with one or more lower-valent cations in the B position or with a mixture of different B elements in the B position, characterized in that said one or more lower-valent cations are selected from Mg, Sc, Y, Nd or Yb; and
   one or more $A_2B_2O_7$-pyrochlores with A tri-valent cation and B tetra-valent cation being at least partially substituted in A position with one or more lower-valent cations and comprising at least one of Sn, Zr and Ti in B position, characterized in that said one or more lower-valent cations are selected from Ca or Mg.

8. The process according to claim 1, characterized in that the electrically conductive particles of the bed are or comprise one or more metallic alloys.

9. The process according to claim 1, characterized in that the electrically conductive particles of the bed are or comprise one or more superionic conductors selected from the group consisting of $LiAlSiO_4$, $Li_{10}GeP_2S_{12}$, $Li_{3.6}Si_{0.6}P_{0.4}O_4$, sodium superionic conductors, and sodium beta alumina.

10. The process according to claim 1, characterized in that the process is selected from a paraffin dehydrogenation process, an alkyl-aromatic dehydrogenation process, a naphtha reforming process and a paraffin aromatization process.

11. The process according to claim 1, characterized in that said process is a paraffin dehydrogenation process and in that said one or more catalytic support is one or more refractory materials.

12. The process according to claim 11, characterized in that the step c) of heating the fluidized bed to a temperature ranging from 480° C. to 700° C. to conduct the endothermic dehydrogenation and/or aromatization of hydrocarbons further comprises the sub step of recovering the particles from the reaction zone and recycling them to the heating zone.

13. The installation according to claim 12, characterized in that the installation further comprises a desulfurization reactor arranged upstream the fluidized bed reactor.

14. The installation according to claim 13, characterized in that the at least one fluidized bed reactor (18, 19, 37, 39) further comprises means (35) to transport the particles of the bed (25) from the reaction zone (29) back to the heating zone (27).

15. The installation according to claim 13, characterized in that it comprises at least two fluidized bed reactors (37, 39) connected one to each other wherein at least one reactor (37) is the heating zone (27) and at least another reactor (39) is the reaction zone (29).

16. The installation according to claim 13, characterized in that the at least one fluidized bed reactor (19) is a single one fluidized bed reactor wherein the heating zone (27) is the bottom part of the fluidized bed reactor (19) while the reaction zone (29) is the top part of the fluidised bed reactor (19).

17. The installation according to claim 13, characterized in that the at least one fluidized bed (18) comprises at least two lateral zones being an outer zone and an inner zone wherein the outer zone is surrounding the inner zone, with the outer zone being the heating zone (27) and the inner zone being the reaction zone (29).

18. The installation according to claim 12 to perform an endothermic dehydrogenation and/or aromatisation reaction in a process that is a naphtha reforming process or a paraffin aromatisation process, characterized in that the at least one fluidized bed reactor (18, 19, 37, 39) comprises a heating zone (27) and a reaction zone (29), one or more fluid nozzles (23) to provide a reaction fluid to the reaction zone (29).

19. The process according to claim 1, characterized in that, wherein the at least one fluidized bed reactor provided in step a) comprises a heating zone and a reaction zone and wherein the vaporized fluid stream provided in step b) is provided to the heating zone and comprises diluent gases, the step c) of heating the fluidized bed to a temperature ranging from 480° C. to 700° C. to conduct the endothermic dehydrogenation and/or aromatization of hydrocarbons comprises the following sub steps:
heating the fluidized bed to a temperature ranging from 480° C. to 700° C. by passing an electric current at a voltage of at most 100 V through the heating zone of the at least one fluidized bed,
transporting the heated particles from the heating zone to the reaction zone,
in the reaction zone, putting the heated particles in a fluidized state by passing upwardly through the said bed of the reaction zone a fluid stream comprising one or more hydrocarbons and optional diluent gases to obtain a fluidized bed and to conduct the endothermic dehydrogenation and/or aromatization of hydrocarbons.

20. An installation for a process to perform an endothermic dehydrogenation and/or aromatisation reaction, according to claim 1, said installation comprising a vaporizer and at least one fluidized bed reactor (18, 19, 37, 39) arranged downstream the vaporizer, wherein the at least one fluidized bed reactor comprises:
at least two electrodes (13);
a reactor vessel (3);
one or more fluid nozzles (21, 23) for the introduction of a fluidizing gas and/or of a reaction fluid within at least one fluidized bed reactor (18, 19, 37, 39); and
a bed (25) comprising particles;
the installation is characterized in that the particles of the bed (25) comprise electrically conductive particles and particles of a catalytic composition, wherein at least 10 wt. % of the particles based on the total weight of the particles of the bed (25) are electrically conductive particles and have a resistivity ranging from 0.001 Ohm·cm to 500 Ohm·cm at 500° C.; wherein the void fraction of the bed is ranging from 0.5 to 0.8, wherein, the particles of the bed have an average particle size ranging from 5 to 300 µm as determined by sieving according to ASTM D4513-11; wherein the catalytic composition comprises one or more metallic compounds; further wherein the process is a paraffin dehydrogenation process and the catalyst composition comprises one or more catalyst materials selected from the group consisting of gallium, zinc, chromium, iron, metal of the group VIII or mixtures thereof; and one or more catalytic supports; or
that said process is an alkyl-aromatic dehydrogenation process and the catalyst composition comprises from 50 to 85 wt. % of $Fe_2O_3$ based on the total weight of the catalyst composition; from 3 to 25 wt. % of $K_2O$; from 3 to 30 wt. % of $CeO_2$; from 0.1 to 5 wt. % of CaO; from 0.1 to 5 wt. % of $Na_2O$ and from 0.1 to 150 ppm of at least one element selected from Pb, Pt, Os, Jr, Ru, Re, Pd, Ag, Au, Sn or any mixture thereof; or
said process is a naphtha reforming process and the catalyst composition comprises from 0.01 to 3.0 wt. % of one or more metals of the group VIII based on the total weight of the catalyst composition; from 0.1 to 3.5 wt. % of a halide; and from 0.01 to 5.0 wt. % of one or more metals selected from groups IIIA, IVA, IB, VIB and/or VIIB; or
said process is a paraffin aromatisation process and the catalyst composition comprises from 5.0 to 90.0 wt. % of one or more zeolites comprising at least one 10-membered ring channel and based on the total weight of the catalyst composition; from 0.1 to 5.0 wt. % of a halide; and from 0.05 to 10.0 wt. % of one or more catalyst materials selected from the group consisting of Ga, In, Zn, Cu, Re, Mo, and W; or from 0.005 to 1.0 wt. % of one or more metals of the group VIII or mixtures thereof based on the total weight of the catalyst composition.

* * * * *